(12) United States Patent
Lundstrom et al.

(10) Patent No.: US 10,363,112 B2
(45) Date of Patent: *Jul. 30, 2019

(54) SKIN TEAR KIT, INSTRUCTIONAL LABELING SYSTEM, AND METHODS THEREFOR

(71) Applicant: Medline Industries, Inc., Northfield, IL (US)

(72) Inventors: Deanna Lundstrom, Ajaz (CA); Rita Graham, Saskatoon (CA)

(73) Assignee: Medline Industries, Inc., Northfield, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/135,765

(22) Filed: Sep. 19, 2018

(65) Prior Publication Data

US 2019/0015171 A1 Jan. 17, 2019

Related U.S. Application Data

(63) Continuation of application No. 15/206,972, filed on Jul. 11, 2016, now Pat. No. 10,117,718.

(51) Int. Cl.
| | |
|---|---|
| *G09F 3/02* | (2006.01) |
| *A61B 50/30* | (2016.01) |
| *A61F 15/00* | (2006.01) |
| *A61M 35/00* | (2006.01) |
| *A61F 13/40* | (2006.01) |
| *A61F 13/02* | (2006.01) |
| *G09F 3/10* | (2006.01) |

(Continued)

(52) U.S. Cl.
CPC .......... *A61B 50/30* (2016.02); *A61F 13/0206* (2013.01); *A61F 15/001* (2013.01); *A61F 17/00* (2013.01); *A61M 35/003* (2013.01); *A61M 35/006* (2013.01); *G09F 3/02* (2013.01); *G09F 3/10* (2013.01); *A61B 2050/002* (2016.02); *A61B 2050/0065* (2016.02); *A61B 2050/314* (2016.02); *G09F 2003/0241* (2013.01); *G09F 2003/0272* (2013.01)

(58) Field of Classification Search
USPC ............... 206/570, 459.5, 438, 440, 370
See application file for complete search history.

(56) References Cited

U.S. PATENT DOCUMENTS 5,848,700 A * 12/1998 Horn .................. A61F 17/00
206/570
7,398,883 B2 * 7/2008 Tucker .................. A61F 17/00
206/440

(Continued)

*Primary Examiner* — Jacob K Ackun
(74) *Attorney, Agent, or Firm* — Philip H. Burrus, IV

(57) ABSTRACT

A medical kit (100) includes a package (105) having a housing (501) and a lid (103). One or more medical implements (1001,1101,1201,1301) for treating a skin tear wound are arranged in a stacked configuration within the package. An instructional labeling system (106) is coupled to the lid. The instructional labeling system can include an identification (107) of a skin tear type the one or more medical implements are designed to treat, a description (108) of the skin tear type, printed instructions (110) defining one or more steps (111,112,113,114) instructing when to use each medical implement within the package to treat the skin tear wound, and one or more removable adhesive labels (115, 116).

20 Claims, 16 Drawing Sheets

(51) Int. Cl.
*A61F 17/00* (2006.01)
*A61B 50/00* (2016.01)

(56) References Cited

U.S. PATENT DOCUMENTS

| | | | | | |
|---|---|---|---|---|---|
| 7,628,275 | B2* | 12/2009 | Smith | | A62B 99/00 |
| | | | | | 206/232 |
| 7,942,451 | B2* | 5/2011 | Adler | | A61J 7/04 |
| | | | | | 283/81 |
| 8,657,117 | B2* | 2/2014 | Musico | | A63H 33/00 |
| | | | | | 206/232 |
| 2005/0029145 | A1* | 2/2005 | Krackow | | A61M 5/002 |
| | | | | | 206/459.5 |
| 2007/0199848 | A1* | 8/2007 | Ellswood | | A61B 42/40 |
| | | | | | 206/459.5 |
| 2008/0283426 | A1* | 11/2008 | Primer | | A61F 13/8405 |
| | | | | | 206/232 |
| 2009/0152137 | A1* | 6/2009 | Estes | | A61B 50/30 |
| | | | | | 206/232 |
| 2010/0274205 | A1* | 10/2010 | Morelli | | A61M 1/0088 |
| | | | | | 604/290 |
| 2011/0017633 | A1* | 1/2011 | Holstein | | A61F 17/00 |
| | | | | | 206/570 |
| 2011/0024323 | A1* | 2/2011 | Martorano | | A61F 17/00 |
| | | | | | 206/570 |
| 2011/0158565 | A1* | 6/2011 | Hellming | | B65D 31/12 |
| | | | | | 383/203 |
| 2011/0180441 | A1* | 7/2011 | Bach | | G06F 19/326 |
| | | | | | 206/459.5 |
| 2012/0118779 | A1* | 5/2012 | Alipour | | G09F 3/0289 |
| | | | | | 206/459.5 |
| 2012/0141963 | A1* | 6/2012 | Singh | | B65D 5/4216 |
| | | | | | 434/262 |
| 2012/0185276 | A1* | 7/2012 | Shah | | A61M 15/009 |
| | | | | | 705/3 |
| 2015/0272826 | A1* | 10/2015 | Alonso | | A61J 1/035 |
| | | | | | 206/459.5 |
| 2016/0030261 | A1* | 2/2016 | Martin | | A61F 17/00 |
| | | | | | 206/570 |

* cited by examiner

SKIN TEAR KIT, INSTRUCTIONAL LABELING SYSTEM, AND METHODS THEREFOR

CROSS REFERENCE TO PRIOR APPLICATIONS

This application is a continuation application claiming priority and benefit under 35 U.S.C. § 120 from U.S. application Ser. No. 15/206,972, filed Jul. 11, 2016, which is incorporated by reference for all purposes.

BACKGROUND

Technical Field

This disclosure relates generally to first aid kits, and more particularly to kits for treating skin tears.

Background Art

Healthcare facilities are increasingly concerned about the occurrence of secondary complications occurring during medical procedures. For example, a person who suffers from a laceration may be susceptible to contracting a secondary infection or other malady if the wound is not treated properly. Moreover, lacerations and skin tears are generally classified into three types. However, it medical personnel are unable to classify a particular wound into one of the three types, treatment may be ineffective, thereby leading to secondary complications. Even if a wound is properly classified, medical personnel may not have experience treating such a wound. This, too, can lead to secondary complications. It would be advantageous to have improved medical kits and associated methods and systems that help to prevent secondary complications associated with skin tears and other similar wounds.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present disclosure.

Figure 1:
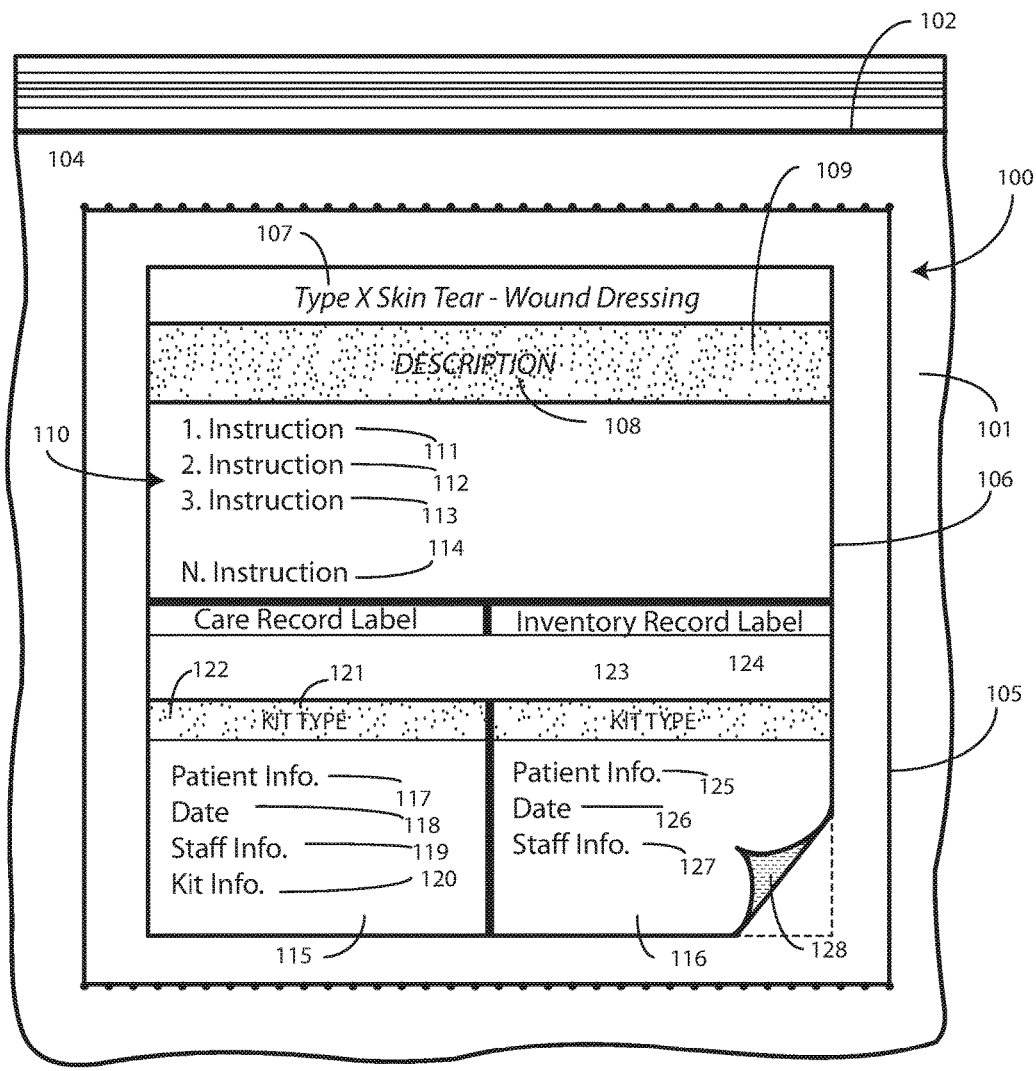
FIG. 1 illustrates one explanatory medical kit in accordance with one or more embodiments of the disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION OF THE DRAWINGS

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. The terms "about" or "substantially" refer to items inclusive of manufacturing tolerances. Accordingly, a length of "about ten inches," where the manufacturing tolerances were plus or minus two tenths of an inch, would include the range 9.8 to 10.2 inches, inclusive. Also, reference designators shown herein in parenthesis indicate components shown in a figure other than the one in discussion. For example, talking about a device (10) while discussing figure A would refer to an element, 10, shown in figure other than figure A.

Skin tears are the result of trauma that lacerates the skin. Skin tears cause pain and suffering. Skin tears are generally classified into three types. The first type is where no skin loss occurs and the flap can be repositioned atop the wound bed. The second type is where partial flap loss occurs, and the flap cannot be positioned over the entire wound bed. This second type can be sub-classified into wounds that have little or no drainage and wounds that have moderate to heavy drainage. The third type is where total flap loss occurs such that no skin can be repositioned atop the wound bed.

Frequently, medical personnel are unaware of these classifications. As such, medical personnel can be unaware that the best practice recommendations for treating each class, such as those developed by Kim LeBlanc et al., and employed the Registered Nurses Association of Ontario (RNAO), differ. Accordingly, medical personnel are sometimes unaware of how to use appropriate products, or categories of product, to treat the various types of skin tears. Even those medical personnel who are aware of the different types of skin tears may be unable to properly classify a particular wound into its appropriate class. These deficiencies can lead to improper or ineffective treatment, which can lead to secondary complications such as infection, pressure ulcers, and the like.

Embodiments of the disclosure contemplate that there is a need to help medical personnel to be able to properly assess skin tears and treat and manage them in accordance with best practice recommendations such as those employed by the RNAO. Moreover, embodiments of the disclosure contemplate that there is a need to provide such medical personnel with not only a compact medical kit with exactly the correct medical implements to treat a particular wound class, but to provide educational material that is functionally related to the implements disposed within the kit to teach those medical personnel how to use the various implements, in a particular order, to properly manage skin tears.

Accordingly, embodiments of the disclosure provide a medical kit that helps to educate medical personnel in how to classify skin tears, what medical implements to use to treat a skin tear once classified, and how to use those medical implements when treating the skin tear. In one or more embodiments, each medical kit is equipped with an instructional labeling system, which is directly functionally related to the medical kit to which it is adhered, that teaches skin tear classification, provides instructions for which kit and/or medical implements to select for a wound once classified, provides instructions regarding how to use those medical implements to properly treat the wound, and provides protocols for treating skin tears that meet best practice recommendations to ensure that wound healing is optimized and secondary complications are avoided.

In one embodiment, each medical kit is disposed within an exterior packaging such as a sealed plastic bag. The medical kit disposed within the bag is then packaged in a housing with a peelable lid. In one or more embodiments, the medical kits are not sterilized because they do not need to be due to the fact that skin tear wound treatment is performed with an aseptic technique.

In one embodiment, an instructional labeling system is attached to the peelable lid. The instructional labeling system includes information regarding how to classify skin tears and whether the particular medical kit is suitable for treating a particular type of skin tear. The instructional labeling system may also include notations regarding wound drainage for wounds such as Type 2 wounds that may be sub-classified into wounds that have little or no drainage and wounds that have moderate to heavy drainage. In one embodiment, these descriptions of wound types are defined by the International Skin Tear Advisory Panel (ISTAP) in accordance with their 2014 standards. This, as well as the other information described below that is present on the instructional labeling system, helps to solve the problem of medical personnel being unable to properly identify and classify skin tears.

In one or more embodiments, the instructional labeling system further includes step-by-step instructions for cleansing and treating a particular wound in accordance with a best practice recommendation. Inside the medical kit are disposed the medical implements required to treat the wound, thereby eliminating the need for medical personnel to hunt and fish for various medical implements from a stock room to properly treat a wound. In one or more embodiments, these medical implements are arranged, from top to bottom, in accordance with their order of use during a skin tear treatment procedure. Thus, by reading the instructional labeling system, medical personnel are apprised of how the medical implements are arranged within the kit, how to treat a skin tear in accordance with a best practice, and how to use each medical implement in accordance with that best practice.

In one or more embodiments, the instructional labeling system further includes removable adhesive labels that can be used for wound care and inventory records. For example, in one or more embodiments a removable adhesive label includes portions on which a patient's name, treatment date, medical personnel identification, and wound care implements used can be recorded. The removable adhesive label may also identify the type of skin tear and/or the type of skin tear medical kit. This removable adhesive label can be detached from the instructional labeling system and attached to a patient's chart or medical records for easy identification of the treatment that was performed.

In one or more embodiments, the instructional labeling system also includes a removable adhesive label for inventory management. Illustrating by example, in one or more embodiments a removable adhesive label includes a removable adhesive label identifying the type of medical kit from which it came, the patient's name upon whom the medical kit was used, the date the medical kit was used, and an identification of the medical personnel using the medical kit. Advantageously, this removable adhesive label can be attached to inventory records to alert medical staff when replacements need to be procured.

Advantageously, the inclusion of the removable adhesive label upon which the inventory record can be recorded allows wound care prevalence audits to be performed in a timely fashion. Moreover, all wound types occurring at a particular site or facility can be accounted for by using the removable adhesive labels as well. Embodiments of the disclosure contemplate that certain agencies, such as the Ministry of Health and Long Term Care, may require such accountings at medical facilities. Accordingly, this removable label can be used to make audits faster, simpler, cheaper, and less personnel intensive.

In one or more embodiments, each medical kit includes a predefined number of skin tear treatment implements. In one embodiment, each medical kit includes a predefined number of medical implements that correspond with a best practice skin tear treatment protocol described on the instructional labeling system. Accordingly, the instructional labeling system becomes functionally related to the medical implements by its attachment to the packaging as it provides a step-by-step method for using the medical implements disposed within the packaging to treat a skin tear on a patient. In one embodiment, this step-by-step method is specifically correlated to a classification of skin tear. Accordingly, medical personnel are apprised of the exact moment when each medical implement should be used to help reduce the chance of the patient incurring a secondary complication.

In one embodiment, the medical implements disposed within the medical kit are arranged in a stacked configuration. The stack of medical implements is placed within a package. In one embodiment, the package defines an outer surface having a major face. The instructional labeling system can then be attached to the package. In one embodiment, instructional labeling system is also selectively peelable from the outer surface so that it can be removed from the medical kit and used independently.

In one or more embodiments, the instructional labeling system includes medical indicia affixed thereto comprising educational prompts that instruct medical personnel regarding how to use each medical implement disposed within the medical kit. As the medical implements are disposed within the medical kit in a stacked configuration, they can be advantageously placed in the order of use, with each medical implement corresponding to a particular step of the method set forth in the medical indicia and/or educational prompts. This secondarily functions in the prevention of using the medical implements in an improper order.

Embodiments of the disclosure offer numerous advantages over prior art solutions. For example, embodiments of the disclosure contemplate that skin tear protocols are not standardized. Advantageously, instructional labeling systems, which are functionally related and attached to medical kits configured in accordance with embodiments of the disclosure, teach and instruct wound classification and best practice treatment options for treating those wounds. Additionally, the medical kits to which the instructional labeling system is attached include the medical implements, arranged in order of use, for treating the wound in accordance with the best practice treatment procedure. Other advantages will be obvious to those with ordinary skill in the art having the benefit of this disclosure.

Embodiments of the present disclosure work to reduce the risk of secondary complications resulting from skin tears by providing an intuitive medical kit that assists medical personnel in properly classifying skin tears and executing method steps to treat the skin tear wounds and otherwise promote healing of the skin tear while adhering to proper aseptic techniques and best practices. Instructional labeling systems configured in accordance with various embodiments of the disclosure include medical educational and instructional prompts that guide medical personnel through the steps of classifying and treating skin tears while minimizing secondary complication risks.

Advantageously, embodiments of the disclosure overcome problems associated with prior art medical kits. Prior art medical kits do not have medical implements arranged in a logical fashion so as to reduce the chance of secondary complications resulting from skin tears. Moreover, they fail to include the instructional labeling system, with its numerous educational prompts and other indicia offered by embodiments of the present disclosure. As such, they are non-intuitive to use and can require specialized training that few medical personnel possess. These deficiencies result in variation of procedure that can result in improper skin tear treatments that increase the risk of secondary complications.

Advantages offered by the embodiments of the disclosure, as compared to prior art kits, include helping medical personnel more easily classify skin tear wounds and treat the same while minimizing the chance for secondary complications. Moreover, medical kits configured in accordance with one or more embodiments of the disclosure help to ensure medical personnel conformance with proper aseptic techniques. Other advantages and benefits will be obvious to those of ordinary skill in the art having the benefit of this disclosure.

Turning now to FIG. 1, illustrated therein is one explanatory medical kit 100 configured in accordance with one or more embodiments of the disclosure. In this illustrative embodiment, the medical kit 100 is disposed within an exterior packaging 101. In one embodiment, the exterior packaging 101 comprises a plastic bag sealed with a zip-strip closure 102. In other embodiments, the exterior packaging 101 can be a thermally (or otherwise) sealed plastic bag. In still other embodiments the exterior packaging 101 can be omitted.

In one embodiment, the medical kit 100 includes a package 105 having a lid 103 that defines an outer surface. In one embodiment, the lid 103 defines a major face forming the top of the package 105. In one embodiment, the package 105 comprises a housing (shown below with reference to FIGS. 8-13) and the lid 103. In this embodiment, the housing comprises a flexible plastic housing that is sealed with the lid 103. In one embodiment, the lid 103 is a peelable lid that can be removed from the housing by peeling a corner 104 of the lid 103 away from the housing. While this is one example of a compact housing into which various medical implements may be placed, others will be readily obvious to those of ordinary skill in the art having the benefit of this disclosure.

In this illustrative embodiment, the lid 103 seals an interior compartment defined by the housing. In one embodiment, the lid 103 is adhesively sealed together to the housing. Other closure techniques can be used, including fusing, crimping, or thermal bonding.

In this illustrative embodiment the lid 103 is manufactured from a flexible material that is paper-based. However, other types of material can be used, including those that are thermoplastic-based, foil based, or are other types of flexible material. In one or more embodiments, the housing is manufactured from a material that is not permeable to moisture. In still other embodiments, the package can be manufactured from a rigid material, such as a thermoplastic or metal as well. Other packaging configurations will be obvious to those of ordinary skill in the art having the benefit of this disclosure. As will be explained in more detail below, in one or more embodiments, the package 105 can be used to enclose a stacked configuration of medical implements used for treating skin tear wounds. In one embodiment, the package 105 is substantially rectangular when viewed in plan view as shown in FIG. 1. However, it should be noted that the package 105 may take any shape, including square, oval, circular, free-form shapes, or any other desired shape.

Disposed atop the lid 103 is an instructional labeling system 106. In one embodiment the instructional labeling system 106 is manufactured from a flexible material. In this illustrative embodiment, the instructional labeling system 106 is in the form of an adhesive label that is attached to the lid 103 so that it is selectively peelable from the outer surface of the lid 103 so that it can be removed from the medical kit and used independently. However, in other embodiments the instructional labeling system 106 can be permanently affixed to the lid 103. For example, in another embodiment the instructional labeling system 106 can be printed along the lid 103. Other techniques for manufacturing the instructional labeling system 106 will be obvious to those of ordinary skill in the art having the benefit of this disclosure.

The instructional labeling system 106 can include various indicia. In one embodiment, the instructional labeling system 106 includes an identification 107 of the skin tear type it is designed to treat. Examples of such identifications will be described in more detail below with reference to FIGS. 2-5.

In one or more embodiments, the instructional labeling system 106 also includes a description 108 of the skin tear type it is designed to treat. In one embodiment the description 108 includes information regarding how to classify skin tears and whether the particular medical kit is suitable for treating a particular type of skin tear. The description 108 may also include notations regarding wound drainage for wounds. Illustrating by example, if the description 108 is of a Type 2 wound, the description 108 may include notations regarding whether the wound has little or no drainage, or alternatively has moderate to heavy drainage. In one embodiment, these description 108 corresponds to one promulgated by ISTAP in accordance with their 2014 standards. Accordingly, the description 108 can help to solve the problem of medical personnel being unable to properly identify and classify skin tears.

In one embodiment, the description 108 of the skin tear type is disposed along a banner 109. In one embodiment, the banner 109 is color coded to provide a quick identification of the skin tear type that the medical kit 100 is designed to treat. Examples of such color codings and descriptions will be described in more detail below with reference to FIGS. 2-5. In other embodiments, no color coding will be included.

In one or more embodiments, the instructional labeling system 106 also includes printed instructions 110 for treating a particular type of skin tear. In one embodiment, the printed instructions 110 provide step-by-step instructions for cleansing and treating a particular wound in accordance with a best practice procedure. As noted above, in one or more embodiments a number of medical implements required to treat the wound are disposed within the package 105. This advantageously eliminates the need for medical personnel to hunt and fish for various medical implements from a stock room to properly treat a wound. In one or more embodiments, these medical implements are arranged, from top to bottom, in accordance with their order of use during a skin tear treatment procedure. Thus, by reading the printed instructions 110, medical personnel are apprised of how implements are arranged within the medical kit, how to treat a skin tear in accordance with a best practice, and how to use each medical implement in accordance with that best practice.

In one or more embodiments, the printed instructions 110 instruct medical personnel regarding how to clean and treat a skin tear, when to use each medical implement disposed within the package 105, and how to best reduce the chance for causing a secondary complication when treating and managing the skin tear. The printed instructions 110 can include text, pictures, and/or illustrations showing visually how the various steps should be performed as well. Further the printed instructions 110 can notify the medical services provider that the medical implements disposed within the package 105 are ordered corresponding to use during the skin tear treatment procedure prescribed by the printed instructions 110.

In one embodiment, the printed instructions 110 present illustrative instructional material suitable for use in treating skin tears. In one embodiment, the instructional material comprises text only. For example, in the illustrative embodiment of FIG. 1, the instructional material comprises a series of method steps 111,112,113,114. While text is one way to present instructional material on the printed instructions 110, in other embodiments one or more pictorial images can be included with the text to make the printed instructions 110 more easily understandable. As they say, a pictorial image can be worth a thousand words. Accordingly, including one or more pictorial images can reduce the amount of text needed to convey the same message. As will be described in more detail below, in one embodiment a picture of a wound can be included to assist medical personnel in classifying the wound. This allows the medical personnel to select the proper medical kit 100 to treat the wound as well.

In one or more embodiments, the instructional labeling system 106 further includes removable adhesive labels 115, 116 that can be used for wound care and inventory records. For example, in one or more embodiments a first removable adhesive label 115 is used for wound care records. In one embodiment, the first removable adhesive label 115 comprises a patient name portion 117, a date portion 118, a medical personnel portion 119, and a medical kit portion 120. A patient's name can be written in the patient name portion 117, while a date can be written in the date portion 118. The name of medical personnel using the medical kit 100 can be written in the medical personnel portion 119, while information identifying the medical kit or its contents can be written on, or alternatively pre-printed in, the medical kit portion 120. This first removable adhesive label 115 can be detached from the instructional labeling system 106 and attached to a patient's chart or medical records for easy identification of the treatment that was performed.

In one embodiment, the first removable adhesive label 115 also includes a medical kit identifier 121 identifying the type of medical kit. For example, if the medical kit 100 is a Type 1 Skin Tear kit, these words may be printed as the medical kit identifier 121. In one embodiment, the medical kit identifier 121 is disposed along a colored border 122. In one embodiment, the colored border 122 has a common color with banner 109. In one embodiment this common color allows for easy identification of the type of medical kit. In other embodiments, color will be omitted from the instructional labeling system 106.

In one or more embodiments, the instructional labeling system 106 also includes a second removable adhesive label 116 that can be used for inventory management purposes. In this illustrative embodiment, the second removable adhesive label 116 includes a medical kit identifier 123 identifying the type of medical kit. For example, if the medical kit 100 is a Type 1 Skin Tear kit, these words may be printed as the medical kit identifier 123. In one embodiment, the medical kit identifier 123 is disposed along a colored border 124. In one embodiment, the colored border 124 has a common color with the banner 109 and colored border 122. In one embodiment this common color allows for easy identification of the type of medical kit. In other embodiments, color will be omitted from the instructional labeling system 106.

In one embodiment, the second removable adhesive label 116 identifies not only the type of medical kit from which it came, but also the patient's name upon whom the medical kit was used, the date the medical kit was used, and an identification of the medical personnel using the medical kit. For example, in this illustrative embodiment the second removable adhesive label 116 comprises a patient name portion 125, a date portion 126, and a medical personnel portion 119. As with the first removable adhesive label 115, a patient's name can be written in the patient name portion 125, while a date can be written in the date portion 126. The name of medical personnel using the medical kit 100 can be written in the medical personnel portion 127. This second removable adhesive label 116 can be detached from the instructional labeling system 106 and attached to inventory records to alert medical staff when replacements need to be procured. The second removable adhesive label 116 is shown in FIG. 1 being peeled away from the instructional labeling system 106, thereby revealing the releasable adhesive 128 disposed along the underside of the second removable adhesive label 116.

Advantageously, the inclusion of the second removable adhesive label 116 upon which the inventory record can be recorded allows wound care prevalence audits to be performed in a timely fashion. Moreover, all wound types occurring at a particular site or facility can be accounted for by using the removable adhesive labels as well. The inclusion of this second removable adhesive label 116 can be used to make audits faster, simpler, cheaper, and less personnel intensive.

Figure 2:
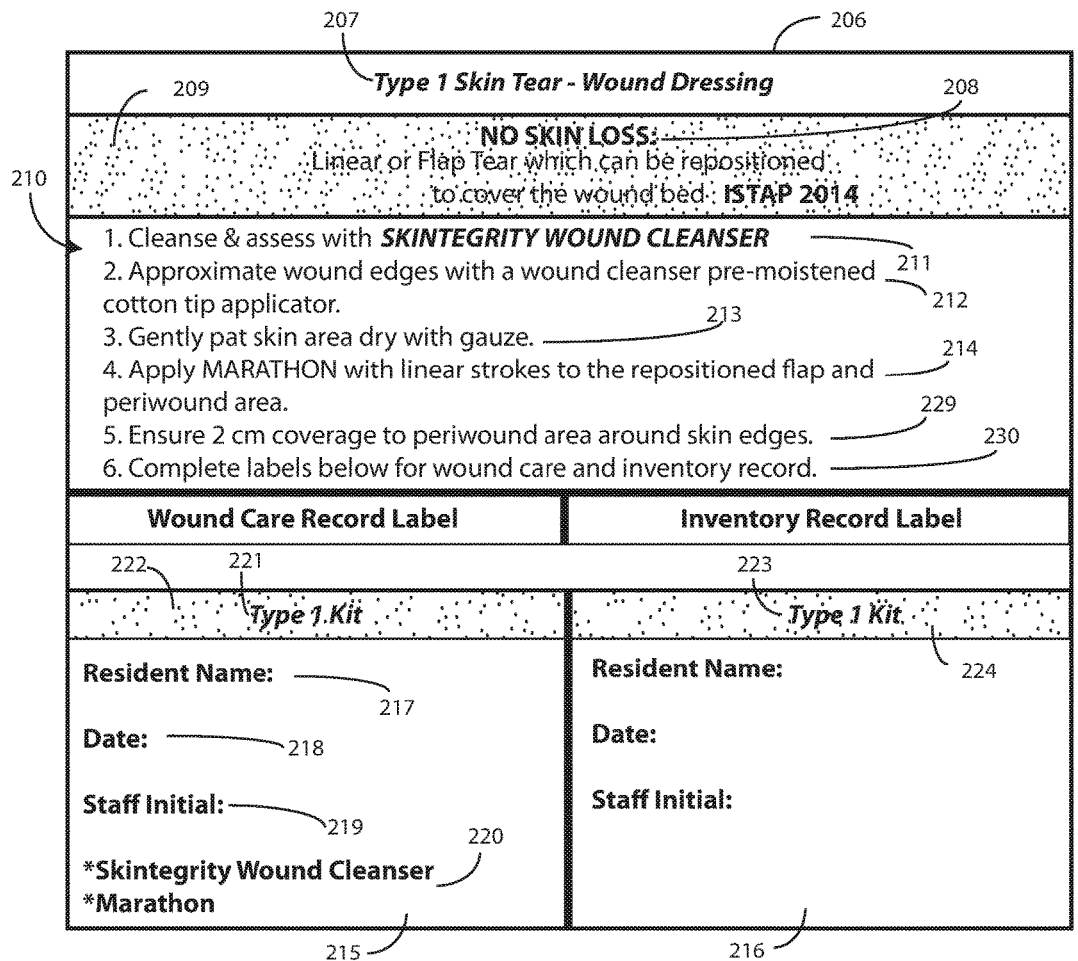
FIG. 2 illustrates one explanatory instructional labeling system for a medical kit in accordance with one or more embodiments of the disclosure.

Turning now to FIG. 2, illustrated therein is an instructional labeling system 206 for a Type 1 skin tear. This illustrative instructional labeling system 206 includes an identification 207 of the skin tear type it is designed to treat. Since this is a Type 1 skin tear, the identification 207 reads, "Type 1 Skin Tear—Wound Dressing." Other identifiers for Type 1 skin tears will be obvious to those of ordinary skill in the art having the benefit of this disclosure.

In this illustrative embodiment, the instructional labeling system 206 also includes a description 208 of the skin tear type it is designed to treat. Since this is a Type 1 skin kit, in this embodiment the description 208 reads, "NO SKIN LOSS: Linear or Flap Tear which can be repositioned to cover the wound bed." In one embodiment, the description 208 also includes a reference to the ISTAP standard with which the description corresponds, which in this case is ISTAP 2014. Other descriptions for Type 1 skin tears will be obvious to those of ordinary skill in the art having the benefit of this disclosure.

Advantageously, the description 208 includes information regarding how to classify skin tears and whether the particular medical kit is suitable for treating a particular type of skin tear. Accordingly, medical personnel can examine a skin tear and read the description 208 to determine if the medical kit is designed to treat the wound. If a person has a linear cut, this would correspond to the description 208. However, if there were no wound flap, this would not correspond to the description. Advantageously, the inclusion of the description 208 helps medical personnel properly classify a wound. Said differently, the inclusion of the description 208 advantageously helps solve the problem of medical personnel being unable to properly identify and classify skin tears.

In this illustrative embodiment, the description 208 of the skin tear type is disposed along a banner 209. In one embodiment, the banner 209 is color coded to provide a quick identification of the skin tear type that the medical kit is designed to treat. Illustrating by example, in this embodiment the banner 209 is purple, which is a color-coding corresponding to Type 1 wounds. Thus, by simply seeing the color purple, medical personnel can quickly identify the medical kit to which the instructional labeling system 206 is attached as a Type 1 skin tear medical kit. It should be noted that color-coding is optional, however. In other embodiments, the banner 209 will be colorless. In still other embodiments the banner 209 will be omitted.

In one or more embodiments, the instructional labeling system 206 also includes printed instructions 210 for treating a particular type of skin tear. In one embodiment, the printed instructions 210 provide step-by-step instructions for cleansing and treating a particular wound in accordance with a best practice procedure. In one or more embodiments, the printed instructions 210 instruct medical personnel regarding how to clean and treat a skin tear, when to use each medical implement disposed within the medical kit to which the instructional labeling system 206 is attached, and how to best reduce the chance for causing a secondary complication when treating and managing the skin tear. Further the printed instructions 210 can notify the medical services provider that the medical implements disposed within the medical kit to which the instructional labeling system 206 is attached are ordered corresponding to use during the skin tear treatment procedure prescribed by the printed instructions 210.

In one embodiment, the printed instructions 210 present illustrative instructional material suitable for use in treating skin tears. In this illustrative embodiment, the instructional material comprises a series of method steps 211,212,213, 214,229,230. In this illustrative embodiment, the first step 211 is to "clean and assess with SKINTEGRITY.sup.™ wound cleanser." In one embodiment, wound cleanser is the first implement disposed within the medical kit to which the instructional labeling system 206 is attached. Accordingly, medical personnel are to retrieve the SKINTEGRITY brand wound cleanser and use the same to clean and assess the wound. While SKINTEGRITY.sup.™ is one suitable brand of wound cleanser, others could be substituted without departing from the spirit and scope of the disclosure.

While SKINTEGRITY.sup.™ can be included within the medical kit, embodiments of the disclosure contemplate that nursing treatment carts are always stocked with normal saline for wound cleansing as a "stock" item. For this reason, in one or more embodiments the SKINTEGRITY.sup.™ skin cleanser will not be included in the medical kit to which the instructional labeling system 206 is attached. Instead, medical personnel will simply use the skin cleanser on their cart instead.

In this illustrative embodiment, the second step 212 is to "approximate the wound edges with a wound cleanser pre-moistened cotton tip applicator." Accordingly, medical personnel are to retrieve a pre-moistened cotton tip applicator from the medical kit and to approximate the wound edges with the same. In one embodiment, this is disposed beneath the wound cleanser in one embodiment so as to be arranged in accordance with the method steps 211,212,213, 214,229,230 of the instructional material. In other embodiments where the skin cleanser is left out, the pre-moistened cotton tip applicator will be an uppermost implement.

In this illustrative embodiment, the third step 213 is to "gently pat skin area dry with gauze." Accordingly, medical personnel are to retrieve packaged gauze from the medical kit to which the instructional labeling system 206 is attached, and dry the skin area. In one embodiment, this gauze would be disposed beneath the pre-moistened cotton tip applicator so as to be arranged in accordance with the method steps 211,212,213,214,229,230 of the instructional material.

In this illustrative embodiment, the fourth step 214 is to "apply MARATHON.sup.™ with linear strokes to the repositioned flap and periwound area." MARATHON.sup.™ is a brand of liquid skin protectant manufactured from a non-cytotoxic cyanoacrylate-based monomer. It resists external moisture, yet allows skin to breath. It acts as medical grade glue that bonds skin together. Accordingly, medical personnel are to retrieve the liquid skin protectant from the medical kit to which the instructional labeling system 206 is attached, and apply it to the wound. In one embodiment, this liquid skin protectant would be disposed beneath the packaged gauze so as to be arranged in accordance with the method steps 211,212,213,214,229,230 of the instructional material. While MARATHON.sup.™ is one suitable brand of skin protectant, others could be substituted without departing from the spirit and scope of the disclosure.

In this illustrative embodiment, the fifth step 229 is to "ensure two centimeter coverage to the periwound area around the skin edges." Accordingly, when using the liquid skin protectant, medical personnel are to ensure that there is coverage of at least two centimeters about the periwound area. In one embodiment, the packaging of the pre-moistened cotton tip applicator can include a ruler so that this coverage can be confirmed.

In this illustrative embodiment, the sixth step 230 is to "complete labels below for wound care and inventory record[s]." As noted above, in one or more embodiments the instructional labeling system 206 further includes removable adhesive labels 215,216 that can be used for wound care and inventory records. In this illustrative embodiment, a first removable adhesive label 215 is used for wound care records, while includes a second removable adhesive label 216 that can be used for inventory management purposes.

In one embodiment, the first removable adhesive label 215 comprises a patient name portion 217, a date portion 218, a medical personnel portion 219, and a medical kit portion 220. A patient's name can be written in the patient name portion 217, while a date can be written in the date portion 218. The name of medical personnel using the medical kit to which the instructional labeling system 206 is attached can be written in the medical personnel portion 219. In this illustrative embodiment, the medical kit portion 220 includes the pre-printed names of the active ingredients used with the kit, i.e., the SKINTEGRITY.sup.™ wound cleanser and the MARATHON.sup.™ liquid skin protectant. This first removable adhesive label 215 can be detached from the instructional labeling system 206 and attached to a patient's chart or medical records for easy identification of the treatment that was performed.

In this embodiment, the first removable adhesive label 215 also includes a medical kit identifier 221 identifying the medical kit to which the instructional labeling system 206 is attached as a Type 1 kit. In this illustrative embodiment, the medical kit identifier 221 is disposed along a colored border 222. In one embodiment, the colored border 222 has a common color with banner 209, which in this case is purple. In one embodiment this common color allows for easy identification of the type of medical kit. In other embodiments, color will be omitted from the instructional labeling system 206.

In this illustrative embodiment, the instructional labeling system 206 also includes a second removable adhesive label 216 that can be used for inventory management purposes. Here the second removable adhesive label 216 includes a medical kit identifier 223 identifying the medical kit to which the instructional labeling system 206 is attached as a Type 1 medical kit. Additionally, in this illustrative embodiment the medical kit identifier 223 is disposed along a colored border 224, which has a common color with banner 209 and colored border 222.

In this illustrative embodiment the second removable adhesive label 216 identifies not only the type of medical kit from which it came, but also the patient's name upon whom the medical kit was used, the date the medical kit was used, and an identification of the medical personnel using the medical kit. This second removable adhesive label 216 can be detached from the instructional labeling system 206 and attached to inventory records to alert medical staff when replacements need to be procured.

Figure 3:
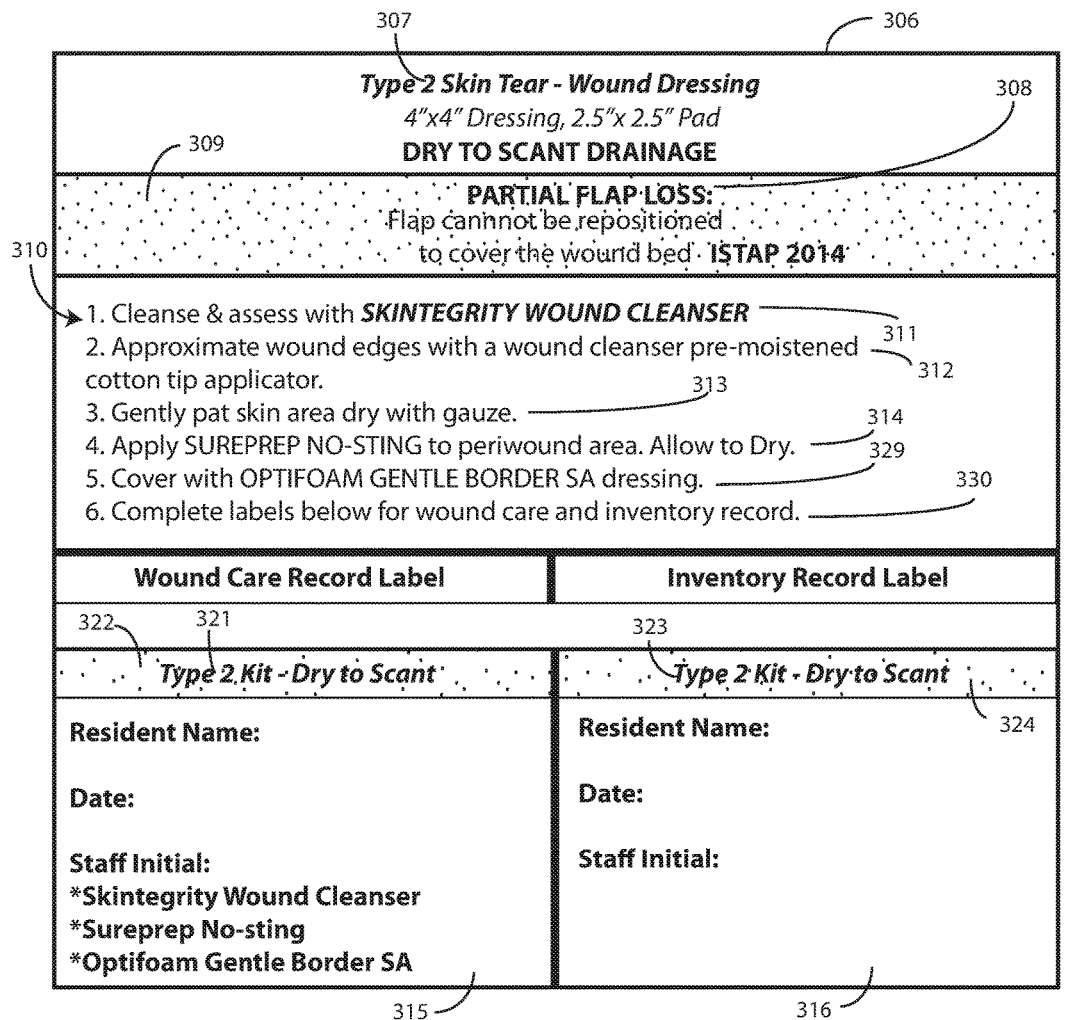
FIG. 3 illustrates another explanatory instructional labeling system for a medical kit in accordance with one or more embodiments of the disclosure.

Turning now to FIG. 3, illustrated therein is an instructional labeling system 306 for a first Type 2 skin tear. This illustrative instructional labeling system 306 includes an identification 307 of the skin tear type it is designed to treat. Since this is a Type 2 skin tear, the identification 307 reads, "Type 2 Skin Tear—Wound Dressing." As noted above, Type 2 kits can be sub-classified into wounds that have little or no drainage and wounds that have moderate to heavy drainage. This first Type 2 kit is for the former. Accordingly, in one embodiment the identification further reads, "Dry to Scant Drainage."

In one or more embodiments, the identification 307 can also include descriptors of the medical implements disposed within the medical kit to which the instructional labeling system 306 is attached. For example, in this illustrative embodiment the identification 307 further comprises, "4"× 4" Dressing, 2.5"×2.5" Pad," thereby alerting medical personnel to the size wound that the medical kit to which the instructional labeling system 306 is attached can treat. Other identifiers for Type 2 skin tears will be obvious to those of ordinary skill in the art having the benefit of this disclosure.

In this illustrative embodiment, the instructional labeling system 306 also includes a description 308 of the skin tear type it is designed to treat. Since this is a Type 2 skin tear kit, in this embodiment the description 308 reads, "PARTIAL FLAP LOSS: Flap cannot be repositioned to cover the wound bed." In one embodiment, the description 308 also includes a reference to the ISTAP standard with which the description corresponds, which in this case is ISTAP 2014. Other descriptions for Type 2 skin tears will be obvious to those of ordinary skill in the art having the benefit of this disclosure.

In this illustrative embodiment, the description 308 of the skin tear type is disposed along a banner 309. In one embodiment, the banner 309 is color coded to provide a quick identification of the skin tear type that the medical kit is designed to treat. Illustrating by example, in this embodiment the banner 309 is orange, which is a color-coding corresponding to Type 2 wounds having little to no drainage. Thus, by simply seeing the color orange, medical personnel can quickly identify the medical kit to which the instructional labeling system 306 is attached as a Type 2 skin tear medical kit for use with non-draining tears.

In one or more embodiments, the instructional labeling system 306 also includes printed instructions 310 for treating a particular type of skin tear. In one embodiment, the printed instructions 310 present illustrative instructional material suitable for use in treating skin tears. In this illustrative embodiment, the instructional material comprises a series of method steps 311,312,313,314,329,330.

In this illustrative embodiment, the first step 311 is to "clean and assess with SKINTEGRITY.sup.™ wound cleanser." Accordingly, medical personnel are to retrieve the SKINTEGRITY brand wound cleanser and use the same to clean and assess the wound.

In this illustrative embodiment, the second step 312 is to "approximate the wound edges with a wound cleanser pre-moistened cotton tip applicator." Accordingly, medical personnel are to retrieve a pre-moistened cotton tip applicator and to approximate the wound edges with the same.

In this illustrative embodiment, the third step 313 is to "gently pat skin area dry with gauze." Accordingly, medical personnel are to retrieve packaged gauze from the medical kit to which the instructional labeling system 306 is attached, and dry the skin area. In one embodiment, this gauze would be disposed beneath the pre-moistened cotton tip applicator so as to be arranged in accordance with the method steps 311,312,313,314,329,330 of the instructional material.

In this illustrative embodiment, the fourth step 314 is to "apply SUREPREP NO-STING.sup.™ to the periwound area. Allow to Dry." SUREPREP NO-STING.sup.™ is a brand of skin protectant applied with a wipe that dries quickly, leaving a long-lasting waterproof coating on the skin to help prevent adhesive trauma and irritation from bodily fluids, incontinence or wound exudate. It includes a patented blend of polymers that form a clear, non-oily protective film when applied to a patient's skin. The polymer blend (along with an acrylic component, which helps it bind to the skin) is dispersed in a water-based solution that allows pain-free application on intact or damaged skin. This skin protectant helps to prevent pain and skin trauma caused by adhesives. It is used to prepare and protect skin before applying tapes, adhesive dressings, or ostomy pouches. In addition, the protectant can help prevent skin damage from wound exudate and other bodily fluids or wastes. Accordingly, medical personnel are to retrieve the liquid skin protectant from the medical kit to which the instructional labeling system 306 is attached, and apply it to the wound. In one embodiment, this liquid skin protectant would be disposed beneath the packaged gauze so as to be arranged in accordance with the method steps 311,312,313,314,329,330 of the instructional material. While SUREPREP NO-STING.sup.™ is one suitable brand of skin protectant, others could be substituted without departing from the spirit and scope of the disclosure.

In this illustrative embodiment, the fifth step 329 is to "Cover with OPTIFOAM GENTLE BORDER SA.sup.™ dressing." OPTIFOAM GENTLE BORDER SA.sup.™ is a foam wound dressing having a silicone adhesive border to minimize damage to skin during dressing changes. Accordingly, medical personnel are to retrieve the wound dressing from the medical kit to which the instructional labeling system 306 is attached, and apply it to the wound. In one embodiment, this wound dressing would be disposed beneath the skin protectant so as to be arranged in accordance with the method steps 311,312,313,314,329,330 of the instructional material. While OPTIFOAM GENTLE BORDER SA.sup.™ is one suitable brand of skin protectant, others could be substituted without departing from the spirit and scope of the disclosure.

In this illustrative embodiment, the sixth step 330 is to "complete labels below for wound care and inventory record[s]." As noted above, in one or more embodiments the instructional labeling system 306 further includes removable adhesive labels 315,316 that can be used for wound care and inventory records. In this illustrative embodiment, a first removable adhesive label 315 is used for wound care records, while includes a second removable adhesive label 316 that can be used for inventory management purposes as previously described.

Figure 4:
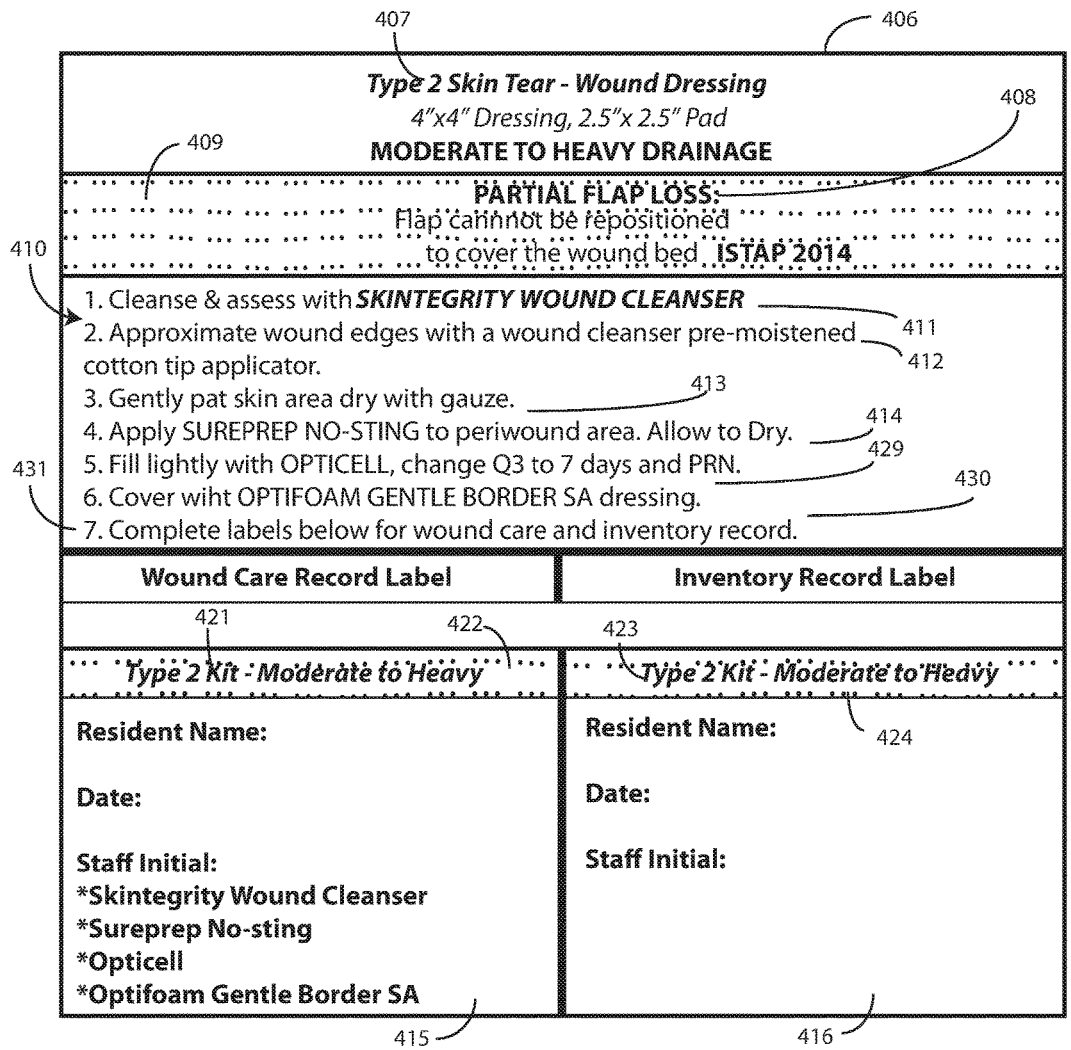
FIG. 4 illustrates yet another explanatory instructional labeling system for a medical kit in accordance with one or more embodiments of the disclosure.

Turning now to FIG. 4, illustrated therein is an instructional labeling system 406 for a second Type 2 skin tear. This illustrative instructional labeling system 406 includes an identification 407 of the skin tear type it is designed to treat. Since this is a Type 2 skin tear, the identification 407 reads, "Type 2 Skin Tear—Wound Dressing." As noted above, Type 2 kits can be sub-classified into wounds that have little or no drainage and wounds that have moderate to heavy drainage. This second Type 2 kit is for the latter. Accordingly, in one embodiment the identification further reads, "Moderate to Heavy Drainage."

In one or more embodiments, the identification 407 can also include descriptors of the medical implements disposed within the medical kit to which the instructional labeling system 406 is attached. For example, in this illustrative embodiment the identification 407 further comprises, "4"× 4" Dressing, 2.5"×2.5" Pad," thereby alerting medical personnel to the size wound that the medical kit to which the instructional labeling system 406 is attached can treat. Other identifiers for Type 2 skin tears will be obvious to those of ordinary skill in the art having the benefit of this disclosure.

In this illustrative embodiment, the instructional labeling system 406 also includes a description 408 of the skin tear type it is designed to treat. Since this is a Type 2 skin tear kit, in this embodiment the description 408 reads, "PARTIAL FLAP LOSS: Flap cannot be repositioned to cover the wound bed." In one embodiment, the description 408 also includes a reference to the ISTAP standard with which the description corresponds, which in this case is ISTAP 2014. Other descriptions for Type 2 skin tears will be obvious to those of ordinary skill in the art having the benefit of this disclosure.

In this illustrative embodiment, the description 408 of the skin tear type is disposed along a banner 409. In one embodiment, the banner 409 is color coded to provide a quick identification of the skin tear type that the medical kit is designed to treat. Illustrating by example, in this embodiment the banner 409 is blue, which is a color-coding corresponding to Type 2 wounds having moderate to high drainage. Thus, by simply seeing the color blue, medical personnel can quickly identify the medical kit to which the instructional labeling system 406 is attached as a Type 2 skin tear medical kit for use with draining tears.

In one or more embodiments, the instructional labeling system 406 also includes printed instructions 410 for treating a particular type of skin tear. In one embodiment, the printed instructions 410 present illustrative instructional material suitable for use in treating skin tears. In this illustrative embodiment, the instructional material comprises a series of method steps 411,412,413,414,429,430, 431.

In this illustrative embodiment, the first step 411 is to "clean and assess with SKINTEGRITY.sup.™ wound cleanser." Accordingly, medical personnel are to retrieve the SKINTEGRITY brand wound cleanser and use the same to clean and assess the wound.

In this illustrative embodiment, the second step 412 is to "approximate the wound edges with a wound cleanser pre-moistened cotton tip applicator." Accordingly, medical personnel are to retrieve a pre-moistened cotton tip applicator and to approximate the wound edges with the same.

In this illustrative embodiment, the third step 413 is to "gently pat skin area dry with gauze." Accordingly, medical personnel are to retrieve packaged gauze from the medical kit to which the instructional labeling system 406 is attached, and dry the skin area. In one embodiment, this gauze would be disposed beneath the pre-moistened cotton tip applicator so as to be arranged in accordance with the method steps 411,412,413,414,429,430,431 of the instructional material.

In this illustrative embodiment, the fourth step 414 is to "apply SUREPREP NO-STING.sup.™ to the periwound area. Allow to Dry." Accordingly, medical personnel are to retrieve the liquid skin protectant from the medical kit to which the instructional labeling system 406 is attached, and apply it to the wound. In one embodiment, this liquid skin protectant would be disposed beneath the packaged gauze so as to be arranged in accordance with the method steps 411,412,413,414,429,430,431 of the instructional material.

In this illustrative embodiment, the fifth step 429 is to "fill lightly with OPTICELL.sup.™, change Q3 to 7 days and PRN." OPTICELL.sup.™ is a wound care dressing using chitosan, a well-known biological material derived from crustacean shells. Chitosan's unique chemistry, including a positive charge at physiological pH, has made it the center of much academic and clinical research. OPTICELL.sup.™ dressings are the first application of this advanced biological material for use in chronic wound care, but chitosan has been used in other health care applications (e.g., topical hemostat, treatment of surgical wounds and traumatic injuries and in dietary supplements) because of its unique properties. When OPTICELL.sup.™ comes into contact with moisture, it transform into a strong, absorbent and conformable gel that controls minor bleeding common in newly debrided wounds. Accordingly, medical personnel are to retrieve the wound dressing from the medical kit to which the instructional labeling system 406 is attached, and use it to lightly fill the wound. In one embodiment, this wound dressing would be disposed beneath the skin protectant so as to be arranged in accordance with the method steps 411, 412,413,414,429,430,431 of the instructional material. While OPTICELL.sup.™ is one suitable brand of dressing, others could be substituted without departing from the spirit and scope of the disclosure.

In this illustrative embodiment, the sixth step 430 is to "cover with OPTIFOAM GENTLE BORDER SA.sup.™ dressing." Accordingly, medical personnel are to retrieve the wound dressing from the medical kit to which the instructional labeling system 406 is attached, and apply it to the wound. In one embodiment, this wound dressing would be disposed beneath the OPTICELL.sup.™ so as to be arranged in accordance with the method steps 411,412,413,414,429, 430,431 of the instructional material.

In this illustrative embodiment, the seventh step 431 is to "complete labels below for wound care and inventory record[s]." As noted above, in one or more embodiments the instructional labeling system 406 further includes removable adhesive labels 415,416 that can be used for wound care and inventory records. In this illustrative embodiment, a first removable adhesive label 415 is used for wound care records, while includes a second removable adhesive label 416 that can be used for inventory management purposes as previously described.

Figure 5:
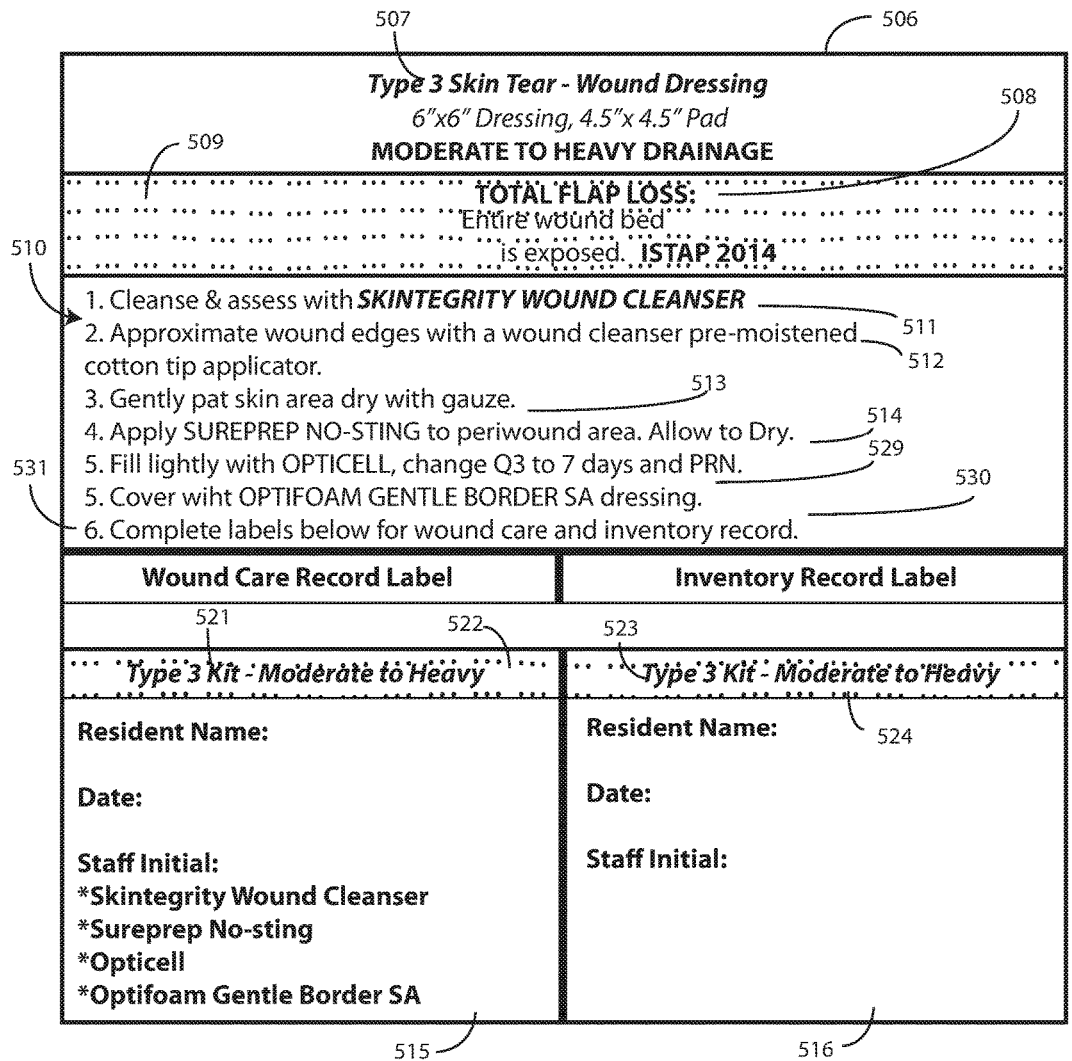
FIG. 5 illustrates still another explanatory instructional labeling system for a medical kit in accordance with one or more embodiments of the disclosure.

Turning now to FIG. 5, illustrated therein is an instructional labeling system 506 for a second Type 3 skin tear. This illustrative instructional labeling system 506 includes an identification 507 of the skin tear type it is designed to treat. Since this is a Type 3 skin tear, the identification 507 reads, "Type 3 Skin Tear—Wound Dressing." As this is a severe skin tear, drainage is expected. Accordingly, in one embodiment the identification 507 further reads, "Moderate to Heavy Drainage."

In one or more embodiments, the identification 507 can also include descriptors of the medical implements disposed within the medical kit to which the instructional labeling system 506 is attached. For example, in this illustrative embodiment the identification 507 further comprises, "6"× 6" Dressing, 4.5"×4.5" Pad," thereby alerting medical personnel to the size wound that the medical kit to which the instructional labeling system 506 is attached can treat. Other identifiers for Type 3 skin tears will be obvious to those of ordinary skill in the art having the benefit of this disclosure.

In this illustrative embodiment, the instructional labeling system 506 also includes a description 508 of the skin tear type it is designed to treat. Since this is a Type 3 skin tear kit, in this embodiment the description 508 reads, "TOTAL FLAP LOSS: Entire wound bed is exposed." In one embodiment, the description 508 also includes a reference to the ISTAP standard with which the description corresponds, which in this case is ISTAP 2014. Other descriptions for Type 3 skin tears will be obvious to those of ordinary skill in the art having the benefit of this disclosure.

In this illustrative embodiment, the description 508 of the skin tear type is disposed along a banner 509. In one embodiment, the banner 509 is color coded to provide a quick identification of the skin tear type that the medical kit is designed to treat. Illustrating by example, in this embodiment the banner 509 is red, which is a color-coding corresponding to Type 3 wounds. Thus, by simply seeing the color red, medical personnel can quickly identify the medical kit to which the instructional labeling system 506 is attached as a Type 3 skin tear medical kit for use with draining tears.

In one or more embodiments, the instructional labeling system 506 also includes printed instructions 510 for treating a particular type of skin tear. In one embodiment, the printed instructions 510 present illustrative instructional material suitable for use in treating skin tears. In this illustrative embodiment, the instructional material comprises a series of method steps 511,512,513,514,529,530, 531.

In this illustrative embodiment, the first step 511 is to "clean and assess with SKINTEGRITY.sup.™ wound cleanser." Accordingly, medical personnel are to retrieve the SKINTEGRITY brand wound cleanser and use the same to clean and assess the wound.

In this illustrative embodiment, the second step 512 is to "approximate the wound edges with a wound cleanser pre-moistened cotton tip applicator." Accordingly, medical personnel are to retrieve a pre-moistened cotton tip applicator and to approximate the wound edges with the same.

In this illustrative embodiment, the third step 513 is to "gently pat skin area dry with gauze." Accordingly, medical personnel are to retrieve packaged gauze from the medical kit to which the instructional labeling system 506 is attached, and dry the skin area. In one embodiment, this gauze would be disposed beneath the pre-moistened cotton tip applicator so as to be arranged in accordance with the method steps 511,512,513,514,529,530,531 of the instructional material.

In this illustrative embodiment, the fourth step 514 is to "apply SUREPREP NO-STING.sup.™ to the periwound area. Allow to Dry." Accordingly, medical personnel are to retrieve the liquid skin protectant from the medical kit to which the instructional labeling system 506 is attached, and apply it to the wound. In one embodiment, this liquid skin protectant would be disposed beneath the packaged gauze so as to be arranged in accordance with the method steps 511,512,513,514,529,530,531 of the instructional material.

In this illustrative embodiment, the fifth step 529 is to "fill lightly with OPTICELL.sup.™, change Q3 to 7 days and PRN." Accordingly, medical personnel are to retrieve the wound dressing from the medical kit to which the instructional labeling system 506 is attached, and use it to lightly fill the wound. In one embodiment, this wound dressing would be disposed beneath the skin protectant so as to be arranged in accordance with the method steps 511,512,513, 514,529,530,531 of the instructional material. It can be changed every three to seven days, as necessary.

In this illustrative embodiment, the sixth step 530 is to "cover with OPTIFOAM GENTLE BORDER SA.sup.™ dressing." Accordingly, medical personnel are to retrieve the wound dressing from the medical kit to which the instructional labeling system 506 is attached, and apply it to the wound. In one embodiment, this wound dressing would be disposed beneath the OPTICELL.sup.™ so as to be arranged in accordance with the method steps 511,512,513,514,529, 530,531 of the instructional material.

In this illustrative embodiment, the seventh step 531 is to "complete labels below for wound care and inventory record[s]." As noted above, in one or more embodiments the instructional labeling system 506 further includes removable adhesive labels 515,516 that can be used for wound care and inventory records. In this illustrative embodiment, a first removable adhesive label 515 is used for wound care records, while includes a second removable adhesive label 516 that can be used for inventory management purposes as previously described.

As noted above, in one or more embodiments, each medical kit includes a predefined number of skin tear treatment implements. In one embodiment, each medical kit includes a predefined number of medical implements that correspond, on a one-to-one basis, with a best practice skin tear treatment protocol described on the instructional labeling system. In other embodiments, additional medical implements, such as drapes or pads, will be included as well. In other embodiments, implements can be omitted. For example, many nurses have skin cleanser readily available. Thus, skin cleanser may be omitted. Of course, combinations of including extra implements and removing others can be used as well. In one or more embodiments all of the medical implements necessary to treat a particular class of skin tear will be included in each medical kit.

In one embodiment, the medical implements disposed within the medical kit are arranged in a stacked configuration. The stack of medical implements is placed within a package. To illustrate this stacked configuration, and the arrangement of medical implements in accordance with their order of use in a skin tear dressing operation, FIGS. 6-13 illustrate various steps of a method to dress Type 3 wound. Accordingly, the medical implements described above with reference to a Type 3 wound will be shown. Only one kit is shown for brevity. However, it should be understood that the method steps of FIGS. 6-13 could be repeated with the Type 2 kits or the Type 1 kits, showing the various medical implements described above, arranged in order of use, rather than those associated with a Type 3 wound. Accordingly, FIGS. 6-13 are illustrative only and are not intended to be limiting.

Figure 6:
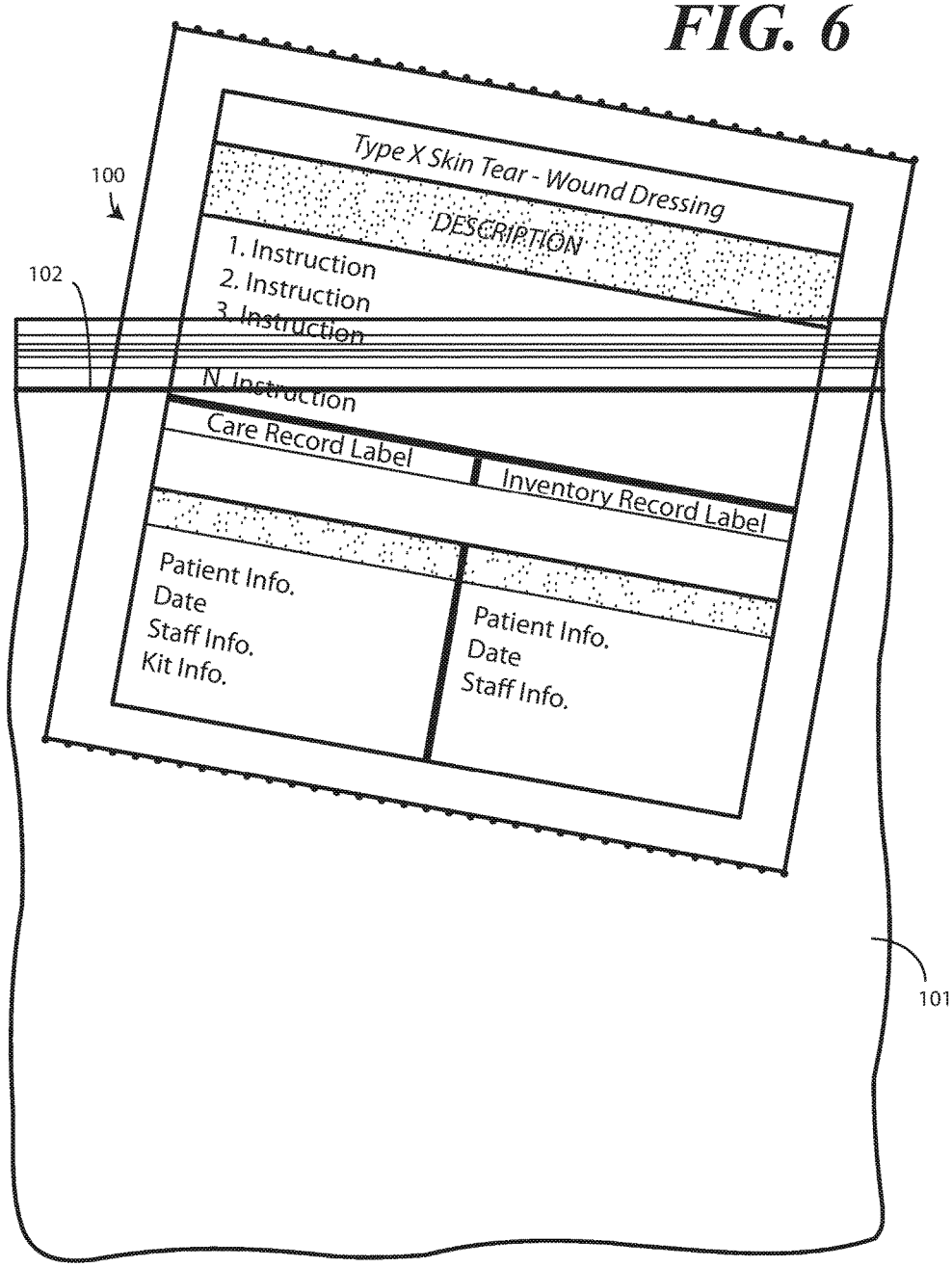
FIG. 6 illustrates one explanatory medical kit, as well as one or more corresponding method steps, in accordance with one or more embodiments of the disclosure.

Beginning with FIG. 6, the medical kit 100 is removed from the optional exterior packaging 101. In one embodiment, the exterior packaging 101 comprises a plastic bag sealed with a zip-strip closure 102. Accordingly, medical personnel open the zip-strip closure 102 and remove the medical kit 100 from the exterior packaging. In other embodiments where the exterior packaging 101 is omitted, the method steps shown in FIG. 6 will be unnecessary.

Figure 7:
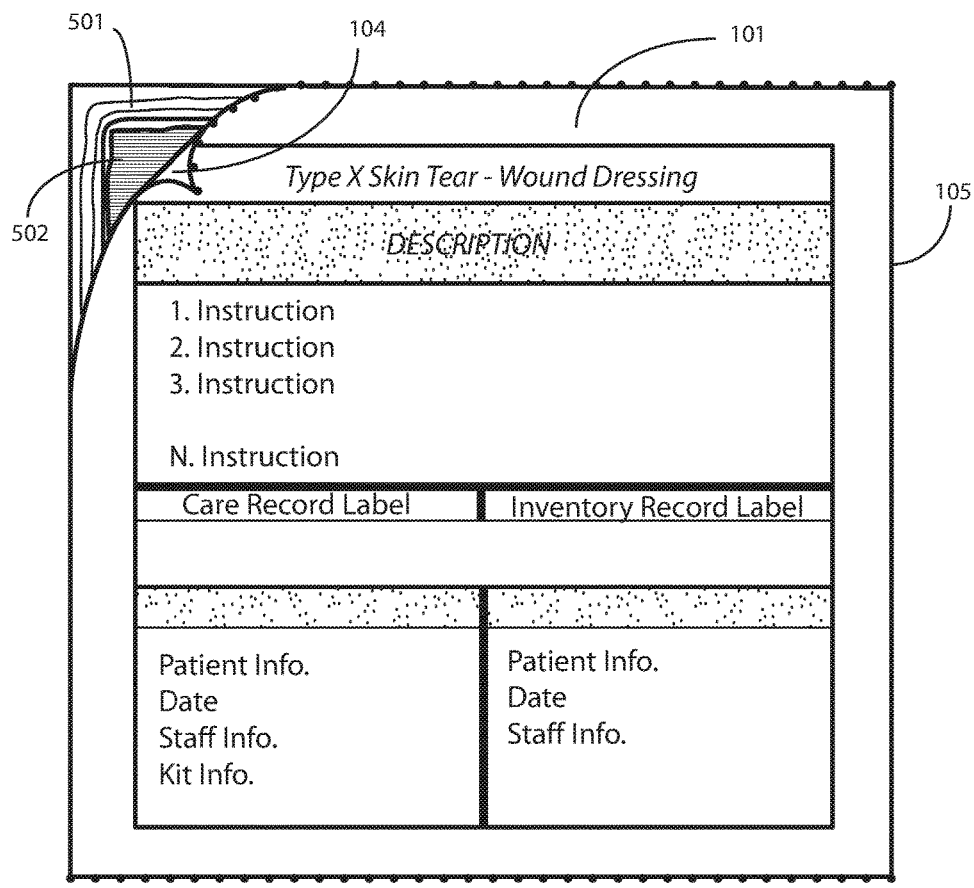
FIG. 7 illustrates one explanatory medical kit, as well as one or more corresponding method steps, in accordance with one or more embodiments of the disclosure.

Turning now to FIG. 7, as shown the medical kit 100 includes a package 105 having a lid 103 and a housing 501. In this embodiment, the housing 501 comprises a flexible plastic housing that is sealed with the lid 103. In this embodiment, the lid 103 is a peelable lid that can be removed from the housing 501 by peeling a corner 104 of the lid 103 away from the housing 501 as shown in FIG. 7.

In this illustrative embodiment, the lid 103 seals an interior compartment 502 defined by the housing 501. In one embodiment, the lid 103 is adhesively sealed together to the housing 501. In one or more embodiments, the package 105 can be used to enclose a stacked configuration of medical implements used for treating skin tear wounds.

Figure 8:
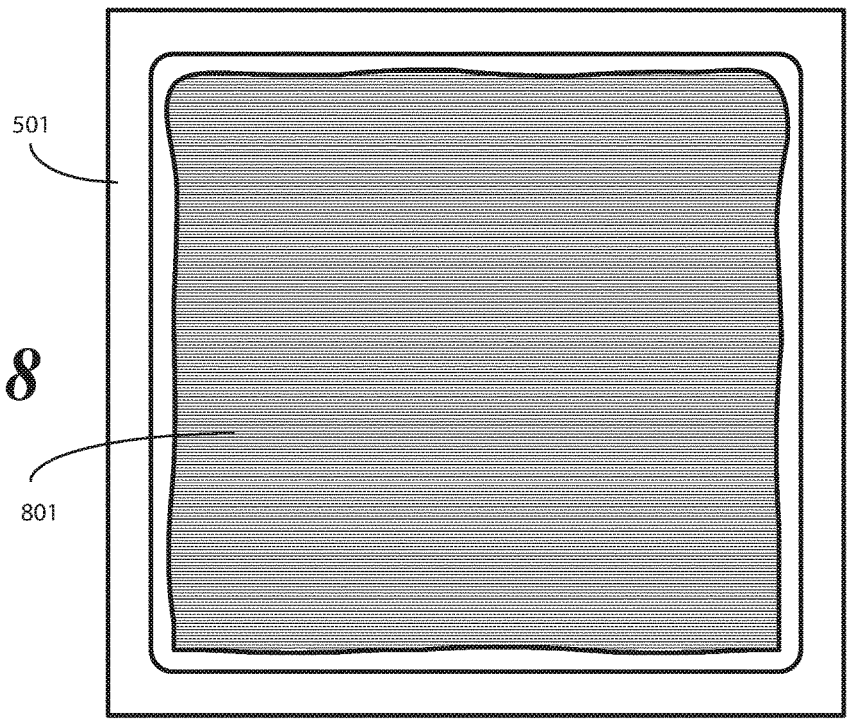
FIG. 8 illustrates one explanatory medical kit, as well as one or more corresponding method steps, in accordance with one or more embodiments of the disclosure.

Turning now to FIG. 8, the lid (103) has been removed. As noted above, combinations of including extra implements and removing others described on the instructional material can be used. For example, many nurses have skin cleanser readily available. Thus, skin cleanser may be omitted. By contrast, medical drapes may not be readily available. Accordingly, they may be included. Such is the case in FIG. 8.

As shown in FIG. 8, a stacked configuration of medical implements is disposed within the housing 501. In this illustrative embodiment, a medical drape 801 is the medical implement disposed atop the stack. The medical drape 801, which can comprise one or more drapes, can be placed under a patient's limb, for example, while the patient is undergoing wound care treatment.

Figure 9:
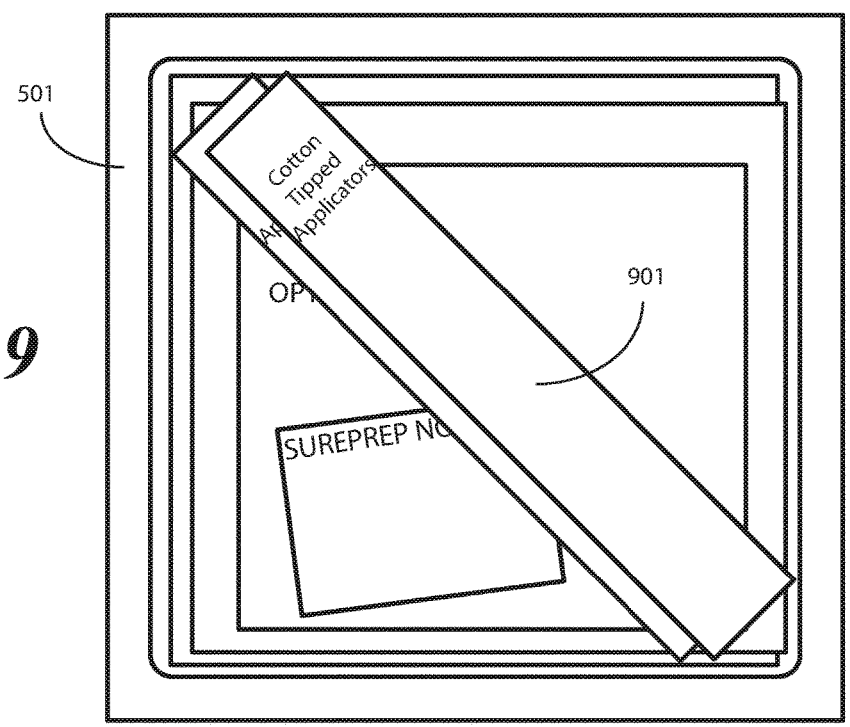
FIG. 9 illustrates one explanatory medical kit, as well as one or more corresponding method steps, in accordance with one or more embodiments of the disclosure.

Turning to FIG. 9, once the medical drape (801) has been removed from the housing, additional medical implements of the stacked configuration can be seen. Recall from above that when treating a Type 3 wound, an instructional labeling system (506) can include printed instructions (510) comprising a series of method steps (511,512,513,514,529,530, 531). In one embodiment, a first step (511) can be to "clean and assess with SKINTEGRITY.sup.™ wound cleanser." As many nurses have wound or skin cleanser readily available, they may access this wound cleanser and use the same to clean and assess the wound.

In one or more embodiments, the second step (512) is to "approximate the wound edges with a wound cleanser pre-moistened cotton tip applicator." As shown in FIG. 9, the second medical implement 901 disposed along the stacked configuration comprises cotton tip applicators. Accordingly, medical personnel are to retrieve a pre-moistened cotton tip applicators to approximate the wound edges.

Figure 10:
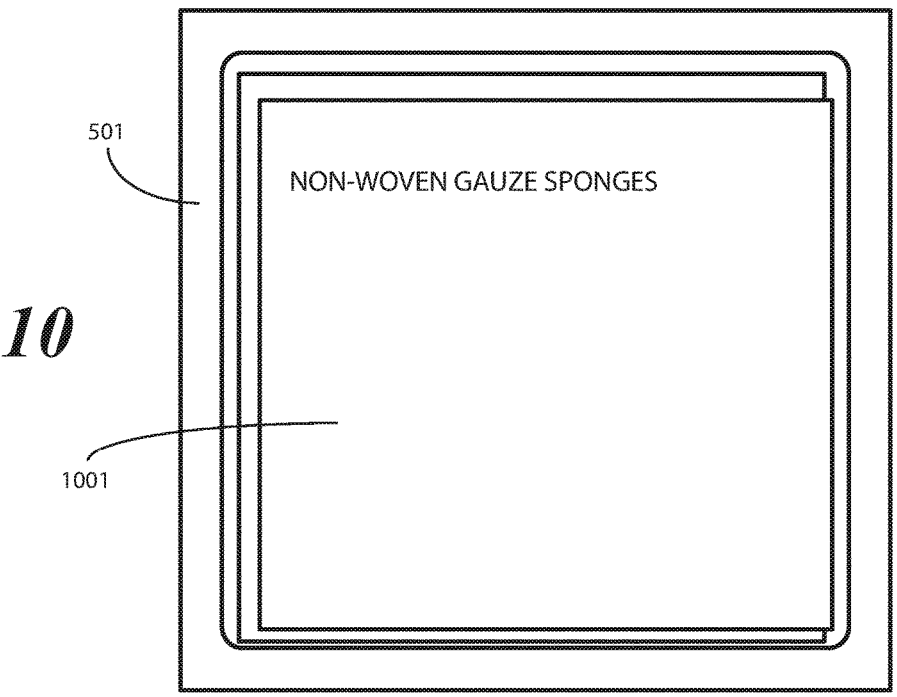
FIG. 10 illustrates one explanatory medical kit, as well as one or more corresponding method steps, in accordance with one or more embodiments of the disclosure.

Turning now to FIG. 10, the cotton tip applicators have been removed from the housing 501. In one embodiment, a third step (513) of treating a wound is to "gently pat skin area dry with gauze." As shown in FIG. 10, the third medical implement 1001 disposed along the stacked configuration packaged gauze. Accordingly, medical personnel are to retrieve packaged gauze from the housing 501 and dry the skin area.

Figure 11:
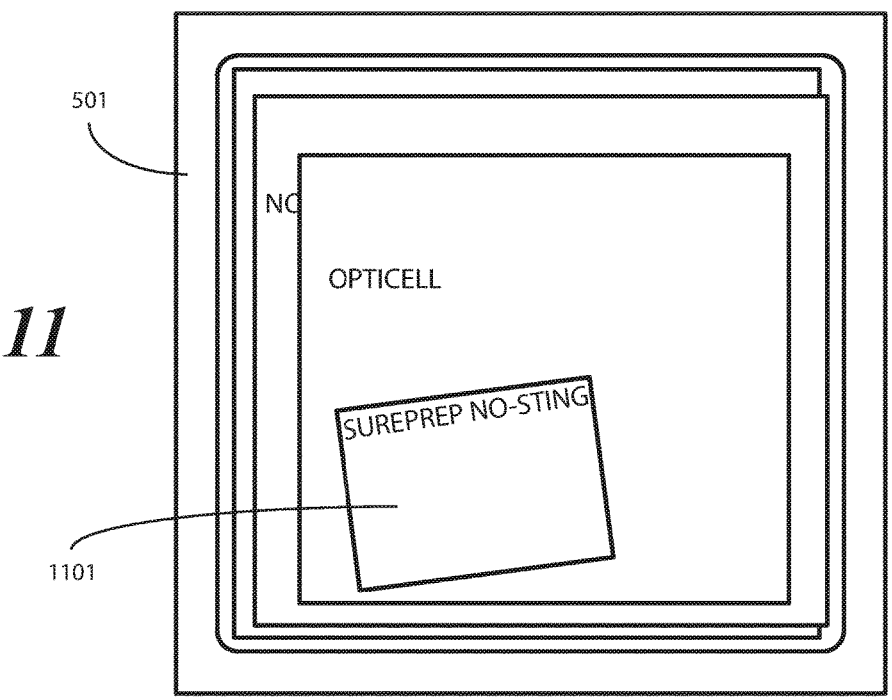
FIG. 11 illustrates one explanatory medical kit, as well as one or more corresponding method steps, in accordance with one or more embodiments of the disclosure.

Turning now to FIG. 11, the gauze has been removed from the housing 501. In one or more embodiments, a fourth step (514) of treating a wound is to "apply SUREPREP NO-STING.sup.™ to the periwound area. Allow to Dry." As shown in FIG. 11, the fourth medical implement 1101 disposed along the stacked configuration liquid skin protectant. Accordingly, medical personnel are to retrieve the liquid skin protectant from the housing 501 and apply it to the wound.

Figure 12:
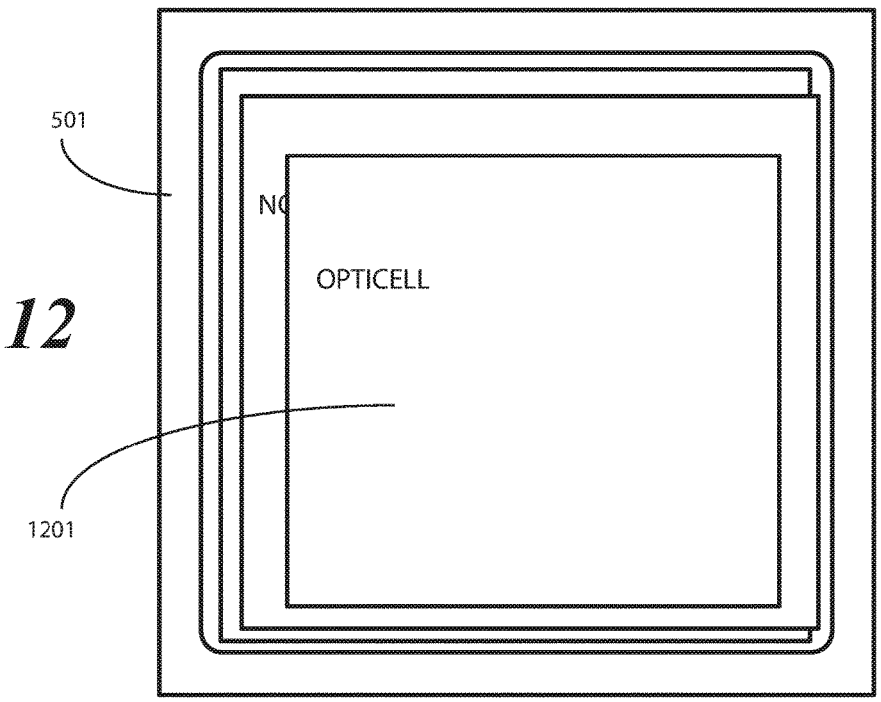
FIG. 12 illustrates one explanatory medical kit, as well as one or more corresponding method steps, in accordance with one or more embodiments of the disclosure.

Turning now to FIG. 12, the liquid skin protectant has been removed from the housing 501. In one embodiment, a fifth step (529) in treating a wound is to "fill lightly with OPTICELL.sup.™, change Q3 to 7 days and PRN." As shown in FIG. 12, the fifth medical implement 1201 disposed along the stacked configuration is the OPTIC-ELL.sup.™ wound dressing. Accordingly, medical personnel are to retrieve the wound dressing from the housing 501 and use it to lightly fill the wound.

Figure 13:
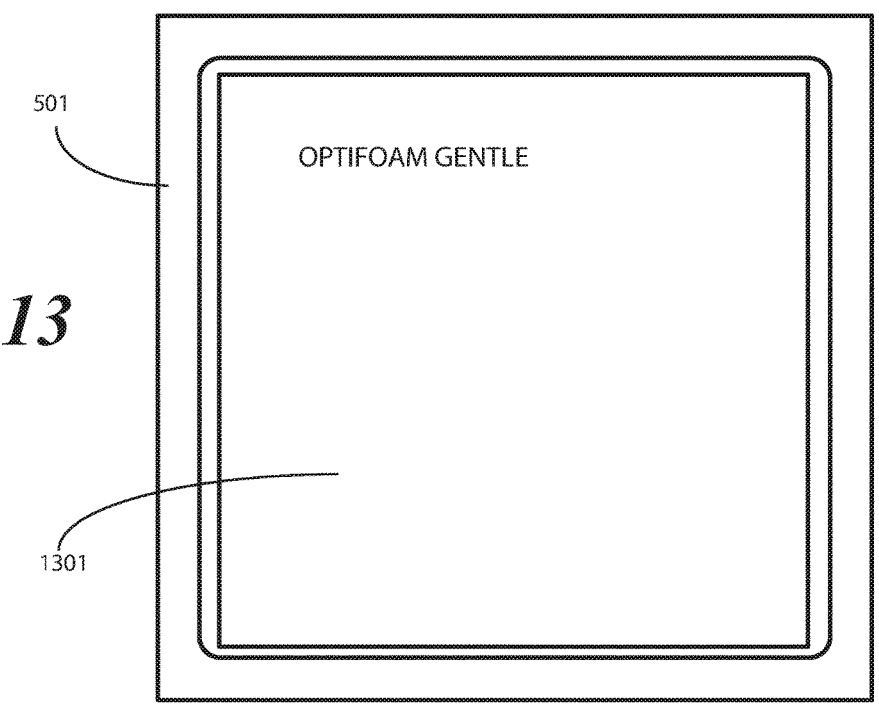
FIG. 13 illustrates one explanatory medical kit, as well as one or more corresponding method steps, in accordance with one or more embodiments of the disclosure.

Turning now to FIG. 13, the OPTICELL.sup.™ wound dressing has been removed from the housing 501. In one embodiment, a sixth step (530) in treating a wound is to "cover with OPTIFOAM GENTLE BORDER SA.sup.™ dressing." As shown in FIG. 13, the sixth medical implement 1301 disposed along the stacked configuration is the OPTI-FOAM.sup.™ wound dressing. Accordingly, medical personnel are to retrieve the wound dressing from the housing 501 and apply it to the wound.

Figure 14:
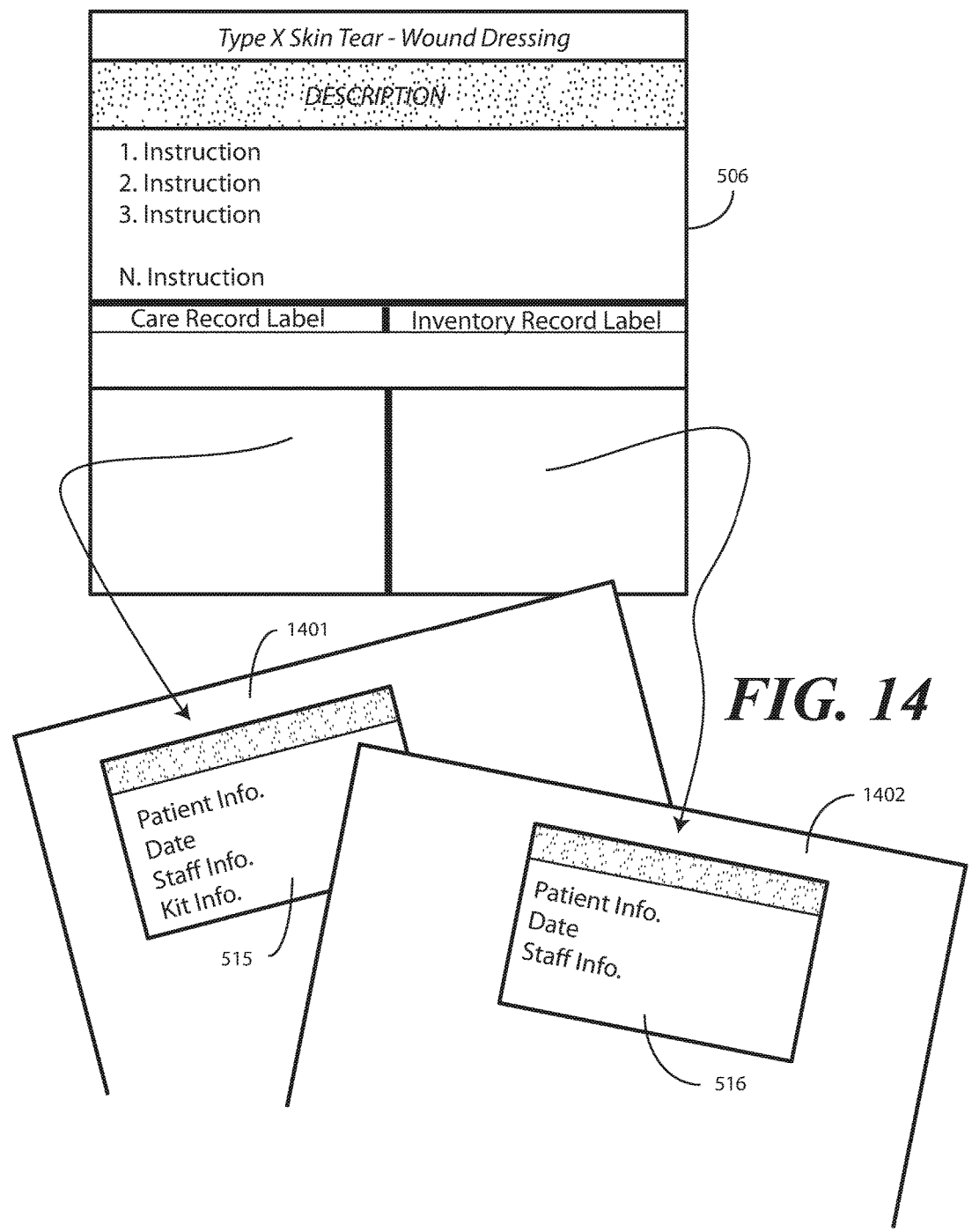
FIG. 14 illustrates one explanatory medical kit, as well as one or more corresponding method steps, in accordance with one or more embodiments of the disclosure.

Turning now to FIG. 14, in one embodiment a final step for treating a wound using medical kits configured in accordance with one or more embodiments of the disclosure is to "complete labels below for wound care and inventory record[s]." As shown in FIG. 14, removable adhesive labels 515,516 have been removed from the instructional labeling system 506 to be used for wound care and inventory records. In this illustrative embodiment, a first removable adhesive label 515 is used for wound care records, while includes a second removable adhesive label 516 that can be used for inventory management purposes.

As shown in FIG. 14, the first removable adhesive label 515 has been detached from the instructional labeling system 506 and attached to a patient's chart 1401 for easy identification of the treatment that was performed. Similarly, the second removable adhesive label 516 has been detached from the instructional labeling system 506 and attached to inventory records 1402 to alert medical staff when replacements need to be procured.

Embodiments of the disclosure contemplate that the instructional labeling system should be customizable for different environments and different applications. For example, the instructional labeling systems described above with reference to FIGS. 2-5 are well suited for medical environments where medical personnel are trained nurses. However, in other environments, such as acute care environments, different types of instructional labeling systems may be preferred.

Figure 15:
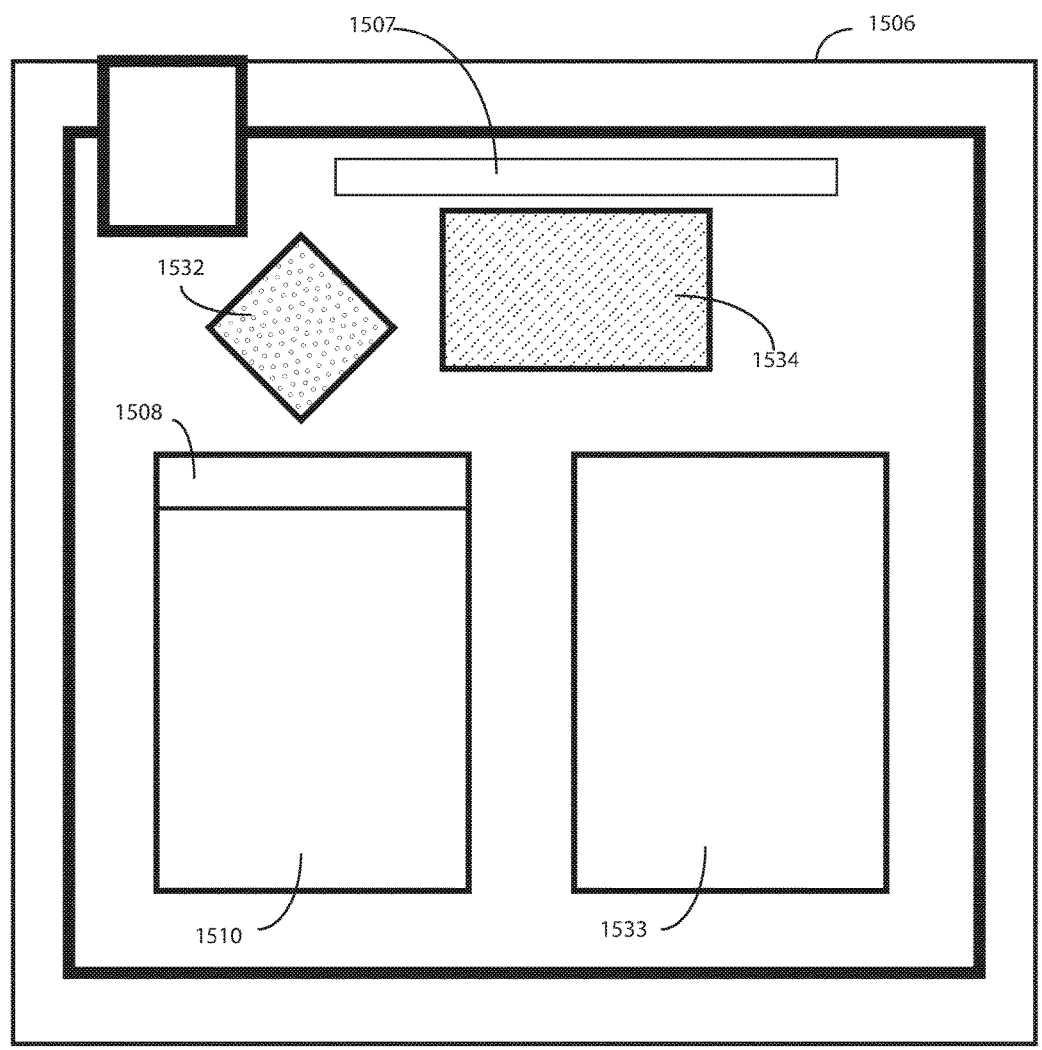
FIG. 15 illustrates an alternate instructional labeling system for a medical kit in accordance with one or more embodiments of the disclosure.

To illustrate the wide range of possibilities embodiments of the disclosure offer, FIGS. 15-18 illustrate alternate instructional labeling systems suitable for use in acute care treatment centers. Beginning with FIG. 15, illustrated therein is one such instructional labeling system 1506. Many of the elements of the instructional labeling system 1506 are the same as those described above with reference to FIGS. 2-5. Accordingly, they will be only briefly discussed—or not discussed at all—in the interest of brevity.

As shown in FIG. 15, the instructional labeling system 1506 can include various indicia. In one embodiment, the instructional labeling system 1506 includes an identification 1507 of the skin tear type it is designed to treat. Examples of such identifications are shown below with reference to FIGS. 16-18.

In one or more embodiments, an indicator badge 1532 may also be included to identify the skin tear type that the medical kit to which the instructional labeling system 1506 is attached is designed to treat. In one or more embodiments, the indicator badge 1532 is configured as a diamond with a large Arabic numeral disposed thereon. For example, if the medical kit to which the instructional labeling system 1506 is attached is a Type 1 kit, the indicator badge 1532 may be a diamond with a large number "1" on it. Similarly, if the medical kit to which the instructional labeling system 1506 is attached is a Type 2 kit, the indicator badge 1532 may be a diamond with a large number "2" on it. The indicator badge 1532 may additionally be color-coded as were the banners described above.

In one or more embodiments, the instructional labeling system 1506 also includes a description 1508 of the skin tear type it is designed to treat. In one embodiment the description 1508 includes information regarding how to classify skin tears and whether the particular medical kit is suitable for treating a particular type of skin tear. The description 1508 may also include notations regarding wound drainage for wounds. Illustrating by example, if the description 1508 is of a Type 2 wound, the description 1508 may include notations regarding whether the wound has little or no drainage, or alternatively has moderate to heavy drainage. In one embodiment, these description 1508 corresponds to one promulgated by ISTAP in accordance with their 2014 standards. Accordingly, the description 1508 can help to solve the problem of medical personnel being unable to properly identify and classify skin tears.

In one or more embodiments, the instructional labeling system 1506 also includes printed instructions 1510 for treating a particular type of skin tear. In one embodiment, the printed instructions 1510 provide step-by-step instructions for cleansing and treating a particular wound in accordance with a best practice procedure. As noted above, in one or more embodiments a number of medical implements required to treat the wound are disposed within the medical kit to which the instructional labeling system 1506 is attached. By reading the printed instructions 1510, medical personnel are apprised of how implements are arranged within the medical kit, how to treat a skin tear in accordance with a best practice, and how to use each medical implement in accordance with that best practice.

In one or more embodiments, the printed instructions 1510 instruct medical personnel regarding how to clean and treat a skin tear, when to use each medical implement disposed within the package 1505, and how to best reduce the chance for causing a secondary complication when treating and managing the skin tear. The printed instructions 1510 can include text, pictures, and/or illustrations showing visually how the various steps should be performed as well. Further the printed instructions 1510 can notify the medical services provider that the medical implements disposed within the medical kit to which the instructional labeling system 1506 is attached are ordered corresponding to use during the skin tear treatment procedure prescribed by the printed instructions 1510. Examples of the printed instructions 1510 are shown below in FIGS. 16-18.

To accommodate multilingual practice, in one embodiment the instructional labeling system 1506 also includes a translation 1533 of the printed instructions 1510. For example, if the printed instructions 1510 are in English, the translation 1533 of the printed instructions 1510 may be in French. The translation 1533 can comprise other languages as well. Examples of the translations 1533 are shown below in FIGS. 16-18.

In one or more embodiments, the instructional labeling system 1506 can also include one or more pictorial images 1534 to make the printed instructions 110 more easily understandable. As they say, a pictorial image can be worth a thousand words. Accordingly, including one or more pictorial images 1534 can reduce the amount of text needed to convey the same message.

In one embodiment, the pictorial images 1534 comprise a picture of a wound to assist medical personnel in classifying the wound. This allows the medical personnel to select the proper medical kit to which the instructional labeling system 1506 is attached to treat the wound as well.

Figure 16:
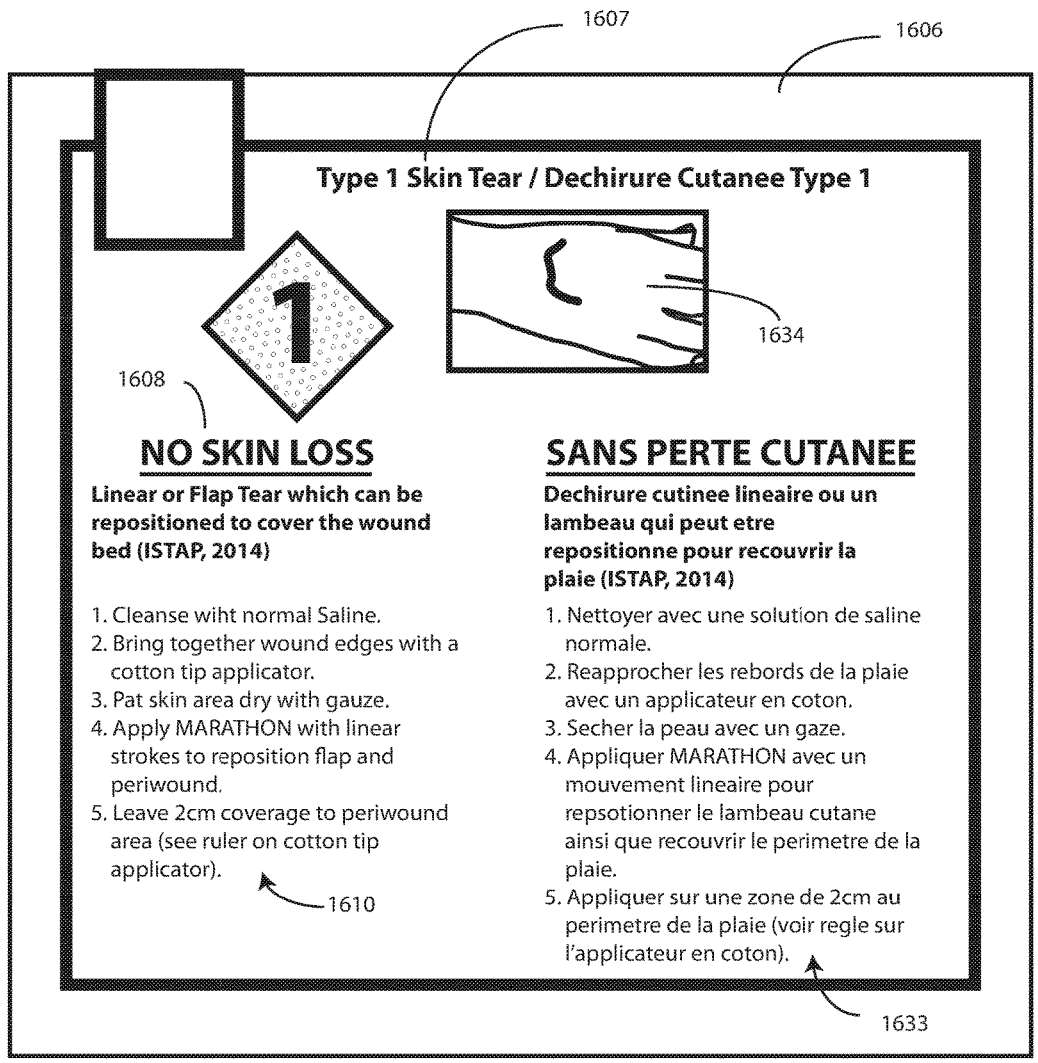
FIG. 16 illustrates another explanatory instructional labeling system for a medical kit in accordance with one or more embodiments of the disclosure.
Figure 17:
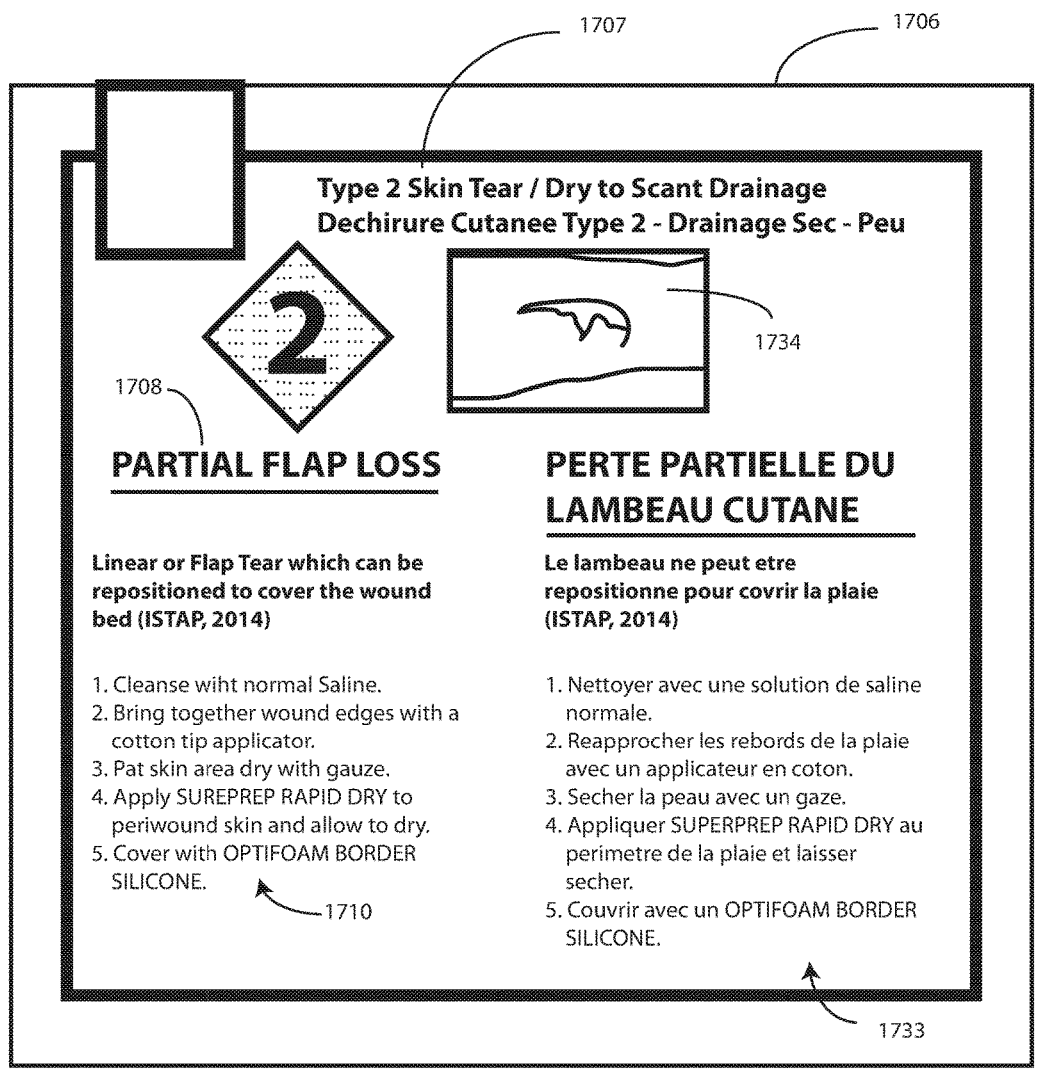
FIG. 17 illustrates another explanatory instructional labeling system for a medical kit in accordance with one or more embodiments of the disclosure.
Figure 18:
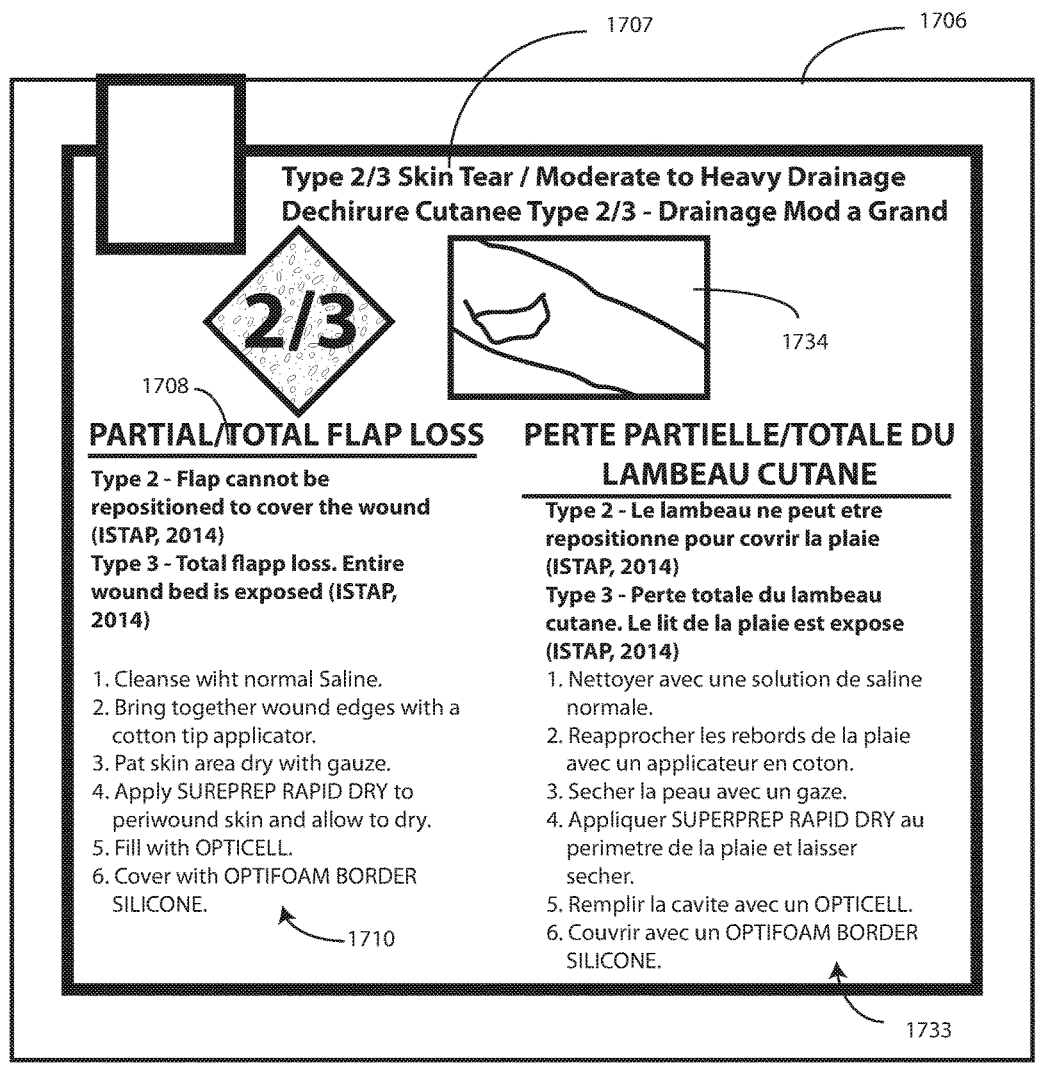
FIG. 18 illustrates yet another explanatory instructional labeling system for a medical kit in accordance with one or more embodiments of the disclosure.

Turning to FIGS. 16-18, illustrated therein are various instructional labeling systems. Beginning with FIG. 16, an instructional labeling system 1606 is for a Type 1 skin tear. Accordingly, the badge 1632 is color-coded and includes a large number "1." Additionally, the pictorial image 1634 of a person's hand with a Type 1 skin tear. The translation 1633 is in French, as the printed instructions 1610 are in English. The description 1607, identifier 1608, and printed instructions 1610 for the Type 1 wound are as described above with reference to FIG. 2.

Turning to FIG. 17, an instructional labeling system 1706 is for a Type 2 skin tear having little drainage. The badge 1732 is color-coded and includes a large number "2." Additionally, the pictorial image 1734 of a person's leg with a Type 2 skin tear. The translation 1733 is again in French, as the printed instructions 1710 are in English. The description 1707, identifier 1708, and printed instructions 1710 for the Type 2 wound are as described above with reference to FIG. 3.

Turning to FIG. 18, an instructional labeling system 1806 is for a Type 2 skin tear having drainage, or alternatively for a Type 3 skin tear. As noted above, both types of tears are expected to have drainage. Accordingly, in one embodiment the instructional labeling system 1806 can be for a combined Type 2/Type 3 skin tear kit. Accordingly, the badge 1832 can be color-coded red with a large "2/3" disposed thereon. In this illustrative embodiment, the pictorial image 1834 of a person's leg with a Type 3 skin tear. The translation 1833 is again in French, as the printed instructions 1810 are in English. The description 1807 and identifier 1808 can be a combination of those described above with reference to FIGS. 4-5, and as shown in FIG. 18. The printed instructions 1710 are as described above with reference to FIGS. 4-5.

Figure 19:
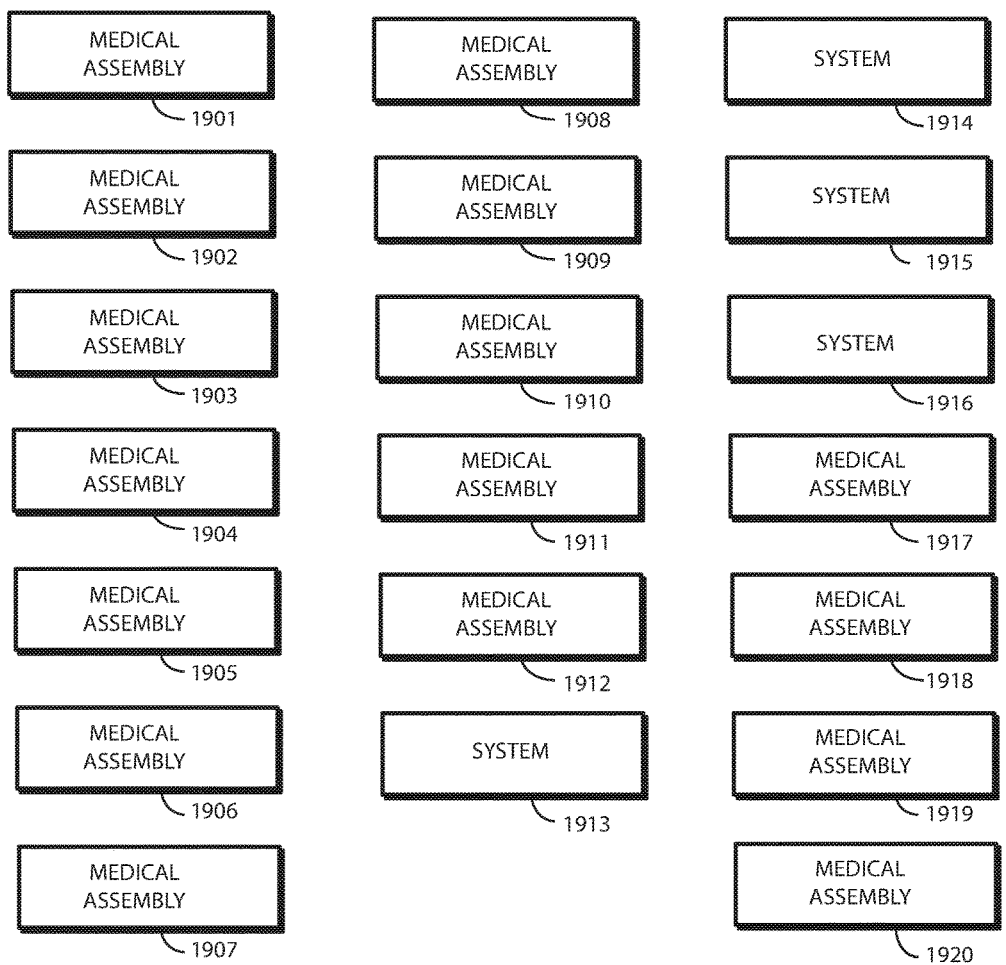
FIG. 19 illustrates various embodiments of the disclosure.

Turning now to FIG. 19, illustrated therein are various embodiments of the disclosure. At 1901, a medical assembly comprises a package comprising a housing and a peelable lid having a major face. At 1901, the medical assembly comprises one or more medical implements for treating a skin tear wound. At 1901, the one or more medical implements are arranged in a stacked configuration within the package. At 1901, the medical assembly comprises an instructional labeling system coupled to the peelable lid.

At 1901, the instructional labeling system comprises an identification of a skin tear type the one or more medical implements are designed to treat. At 1901, the instructional labeling system comprises a description of the skin tear type. At 1901, the instructional labeling system comprises printed instructions defining one or more steps instructing when to use each medical implement within the package to treat the skin tear wound. At 1901, the instructional labeling system also includes one or more removable adhesive labels.

At 1902, the printed instructions of 1901 comprise one or more of pictures or illustrations showing visually how to perform the one or more steps. At 1903, the printed instructions of 1902 indicate that the one or more medical implements are disposed within the package in an order corresponding to use during a skin tear procedure prescribed by the printed instructions.

At 1904, the one or more removable adhesive labels of 1901 comprise a first removable adhesive label and a second removable adhesive label. At 1905, the first removable adhesive label of 1904 comprises a wound care record adhesive label, while the second removable adhesive label comprises an inventory management adhesive label.

At 1906, the skin tear type of 1901 comprises one of a Type 1 skin tear, a Type 2 skin tear, or a Type 3 skin tear. At 1907, the skin tear type of 1906 comprises the Type 2 skin tear, and the description of the Type 2 skin tear comprises a notation regarding whether the skin tear would has drainage. At 1908, the identification of 1906 comprises an indication of an amount of flap loss associated with the skin tear.

At 1909, the skin tear type of 1901 is disposed along a banner. At 1910, the banner is color coded to provide an identification of the skin tear type.

At 1911, the identification of 1901 comprises a descriptor of at least one of the one or more medical implements. At 1912, the one or more medical implements of 1901 comprise gauze. At 1912, the one or more medical implements of 1911 further comprise liquid skin protectant. At 1912, the one or more medical implements of 1911 further comprise one or more cotton tip applicators. At 1912, the one or more medical implements of 1911 further comprise a wound dressing comprising chitosan. At 1912, the one or more medical implements of 1911 further comprise a foam wound dressing having a silicone adhesive border.

At 1913, a system comprises a plurality of medical kits. At 1913, each medical kit of the system comprises implements to treat a common wound type, wherein a first medical kit comprises first implements to treat a first level of the common wound type and a second medical kit comprises second implements to treat a second level of the common wound type.

At 1913, each medical kit comprises an instructional labeling system coupled to an exterior of the each medical kit. At 1913, the instructional labeling system comprises an identification of a level of the common wound type the implements are designed to treat. At 1913, the instructional labeling system comprises a description of the level of the common wound type. At 1913, the instructional labeling system comprises printed instructions defining one or more steps instructing when to use each implement within the each medical kit to treat the level of the common wound type. At 1913, the instructional labeling system comprises one or more removable adhesive labels.

At 1914, the one or more removable adhesive labels of 1913 comprises a wound care record adhesive label, while the second removable adhesive label comprising an inventory management adhesive label. At 1915, the common wound type of 1913 comprises one of a skin tear, a pressure ulcer, a skin abrasion, or combinations thereof. At 1916, the common wound type of 1913 is disposed along a banner of the instructional labeling system, wherein the banner is color coded to provide an identification of a level of the common wound type.

At 1917, a medical assembly comprises a package comprising a housing and lid and one or more medical implements for treating a skin tear wound, arranged in a stacked configuration within the package. At 1917, the medical assembly further comprises an instructional labeling system coupled to the lid. At 1917, the instructional labeling system comprises an identification of a skin tear type the one or more medical implements are designed to treat. At 1917, the instructional labeling system comprises an indicator badge to identify the skin tear type. At 1917, the instructional labeling system comprises a description of the skin tear type. At 1917, the instructional labeling system comprises a pictorial image of the skin tear type. At 1917, the instructional labeling system comprises printed instructions defining one or more steps instructing when to use each medical implement within the package to treat the skin tear wound. At 1917, the instructional labeling system comprises one or more removable adhesive labels.

At 1918, the medical assembly of 1917 comprises a translation of the printed instructions. In one embodiment, this translation is a French translation of English instructions.

At 1919, the indicator badge of 1917 is color coded to provide an identification of the skin tear type. At 1920, the one or more medical implements of 1917 comprise gauze, comprising liquid skin protectant, one or more cotton tip applicators, a wound dressing comprising chitosan, and a foam wound dressing having a silicone adhesive border.

In the foregoing specification, specific embodiments of the present disclosure have been described. However, one of ordinary skill in the art appreciates that various modifications and changes can be made without departing from the scope of the present disclosure as set forth in the claims below. Thus, while preferred embodiments of the disclosure have been illustrated and described, it is clear that the disclosure is not so limited. Numerous modifications, changes, variations, substitutions, and equivalents will occur to those skilled in the art without departing from the spirit and scope of the present disclosure as defined by the following claims. Accordingly, the specification and figures are to be regarded in an illustrative rather than a restrictive sense, and all such modifications are intended to be included within the scope of present disclosure. The benefits, advantages, solutions to problems, and any element(s) that may cause any benefit, advantage, or solution to occur or become more pronounced are not to be construed as a critical, required, or essential features or elements of any or all the claims. The disclosure is defined solely by the appended claims of this application and all equivalents thereof.

What is claimed is:

1. A medical assembly, comprising:
   a package comprising a housing and a peelable lid having a major face; and
   one or more medical implements for treating a wound, arranged in a stacked configuration within the package;
   the peelable lid comprising:
      an identification of a wound type the one or more medical implements are designed to treat;
      a description of the wound type; and
      printed instructions defining one or more steps instructing when to use each medical implement within the package to treat the wound.

2. The medical assembly of claim 1, the printed instructions comprising one or more of pictures or illustrations showing visually how to perform the one or more steps.

3. The medical assembly of claim 2, the printed instructions indicating that the one or more medical implements are disposed within the package in an order corresponding to use during a wound treatment procedure prescribed by the printed instructions.

4. The medical assembly of claim 1, the peelable lid further comprising a first removable adhesive label and a second removable adhesive label.

5. The medical assembly of claim 4, the first removable adhesive label comprising a wound care record adhesive label, the second removable adhesive label comprising an inventory management adhesive label.

6. The medical assembly of claim 1, the wound comprising a skin tear, the skin tear comprising one of a Type 1 skin tear, a Type 2 skin tear, or a Type 3 skin tear.

7. The medical assembly of claim 6, the skin tear comprising the Type 2 skin tear, the description of the Type 2 skin tear comprising a notation regarding whether the skin tear would has drainage.

8. The medical assembly of claim 6, the identification comprising an indication of an amount of flap loss associated with the skin tear.

9. The medical assembly of claim 1, the wound type disposed along a banner.

10. The medical assembly of claim 9, the banner color coded to provide another identification of the wound type.

11. The medical assembly of claim 1, the identification comprising a descriptor of at least one of the one or more medical implements.

12. The medical assembly of claim 1, the one or more medical implements comprising one or more of gauze, liquid skin protectant, one or more cotton tip applicators, a wound dressing comprising chitosan, or a foam wound dressing having a silicone adhesive border.

13. A system comprising:
    a plurality of medical kits, each medical kit comprising implements to treat a common wound type, wherein a first medical kit comprises first implements to treat a first level of the common wound type and a second medical kit comprises second implements to treat a second level of the common wound type;
    wherein an exterior of the each medical kit comprises:
       an identification of a level of the common wound type the implements are designed to treat;
       a description of the level of the common wound type; and
       printed instructions defining one or more steps instructing when to use each implement within the each medical kit to treat the level of the common wound type.

14. The system of claim 13, the exterior further comprising a wound care record adhesive label and an inventory management adhesive label.

15. The system of claim 13, the common wound type comprising one of a skin tear, a pressure ulcer, a skin abrasion, or combinations thereof.

16. The system of claim 13, the common wound type disposed along a banner on the exterior.

17. A medical assembly, comprising:
    a package comprising a housing and lid; and
    one or more medical implements for treating a skin tear wound;
    the lid comprising:
       an identification of a skin tear type the one or more medical implements are designed to treat;
       a pictorial image of the skin tear type; and
       printed instructions defining one or more steps instructing when to use each medical implement within the package to treat the skin tear wound.

18. The medical assembly of claim 17, further comprising a translation of the printed instructions.

19. The medical assembly of claim 17, further comprising an indicator badge to identify the skin tear type.

20. The medical assembly of claim 19, the indicator badge color coded.

* * * * *